United States Patent [19]

Dennis et al.

[11] Patent Number: 5,786,328
[45] Date of Patent: Jul. 28, 1998

[54] USE OF KUNITZ TYPE PLASMA KALLIKREIN INHIBITORS

[75] Inventors: Mark S. Dennis, San Carlos; Robert A. Lazarus, Millbrae, both of Calif.

[73] Assignee: Genentech, Inc., South San Francisco, Calif.

[21] Appl. No.: 463,432

[22] Filed: Jun. 5, 1995

[51] Int. Cl.$^6$ .......................... A61K 38/57; C07K 14/81
[52] U.S. Cl. .............................................. 514/12; 530/350
[58] Field of Search .......................... 530/350; 536/23.5; 435/320.1, 252.3, 69.2; 514/12

[56] References Cited

U.S. PATENT DOCUMENTS

| | | | |
|---|---|---|---|
| 4,894,436 | 1/1990 | Auerswald et al. | 530/324 |
| 5,032,573 | 7/1991 | Auerswald et al. | 514/12 |
| 5,118,668 | 6/1992 | Auerswald et al. | 514/12 |
| 5,164,482 | 11/1992 | Ebbers et al. | 530/324 |
| 5,223,482 | 6/1993 | Schilling, Jr. et al. | 514/12 |
| 5,373,090 | 12/1994 | Norris et al. | 530/324 |

FOREIGN PATENT DOCUMENTS

| | | |
|---|---|---|
| 339942 | 11/1989 | European Pat. Off. . |
| 393431 | 10/1990 | European Pat. Off. . |
| 393431A1 | 10/1990 | European Pat. Off. . |
| 04166087 | 6/1992 | Japan . |
| WO 93/14119 | 7/1993 | WIPO . |
| WO 93/14120 | 7/1993 | WIPO . |
| WO 93/14121 | 7/1993 | WIPO . |
| WO 93/14122 | 7/1993 | WIPO . |
| WO 93/14123 | 7/1993 | WIPO . |
| WO 95/12674 | 5/1995 | WIPO . |
| WO 95/21601 | 8/1995 | WIPO . |
| WO 96/20278 | 7/1996 | WIPO . |

OTHER PUBLICATIONS

Hynes, T.R. et al.(Oct. 1990) "X-ray crystal structure of the protease inhibitor domain of Alzheimer's amyloid beta-protein precursor" Biochem. 29(43):10018–10022.

Kido, H. et al.(Dec. 1988) "Kunitz-type protease inhibitor found in rat mast cells" J. Biol. Chem. 34:18104–18107.

Badimon et al., "Hirudin and Other Thrombin Inhibitors: Experimental Results and Potential Clinical Applications" TCM 1(6):261–267 (1991).

Beckmann, J. et al., "Preparation of chemically 'mutated'aprotinin homologues by semisynthesis" European Journal of Biochemistry 176:675–682 (1988).

Bhoola, K.D. et al., "Bioregulation of Kinins: Kallikreins, Kininogens, and Kininases" Pharmacological Reviews 44(1):1–80 (1992).

Bigler et al., "Binding of amino acid side chains to preformed cavities: Interaction of serine proteinases with turkey ovomucoid third domains with coded and noncoded P1 residues" Protein Science 2:786–799 (1993).

Bode et al., "The refined 2.2-Angstrom (0.22-nm) X-ray crystal structure of the ternary complex formed by bovine trypsinogen, valine-valine and the Arg$^{15}$ analogue of bovine pancreatic trypsin inhibitor" European Journal of Biochemistry 144:185–190 (1984).

Bode, W. et al., "Natural protein proteinase inhibitors and their interaction with proteinases" European Journal of Biochemistry 204:433–451 (1992).

Bone, R.C., "Modulators of Coagulation: A Critical Appraisal of Their Role In Sopsis" Arch Intern Med 152:1381–1389 (1992).

Castro et al., "Does the Kunitz domain from the Alzheimer's amyloid Beta protein precursor inhibit a kallikrein responsible for post–translational processing of nerve growth factor precursor?" FEBS 08591 267(2):207–212 (1990).

Chabbat et al., "Aprotinin Is A Competitive Inhibitor Of The Factor VIIa–Tissue Factor Complex" Thrombosis Research 71:205–215 (1993).

Chu et al., "Mosaic structure of globular domains in the human type VI collagen α 3 chain: similarity to von Willebrand Factor, fibronectin, actin, salivary proteins and aprotinin type protease inhibitors" EMBO Journal 9(2):385–393 (1990).

Creasey et al., "Tissue Factor Pathway Inhibitor Reduces Mortality from Escherichia coli Septic Shock" J. Clin. Invest. 91:2850–2860 (1993).

Creighton et al., "Biosynthesis, Processing, and Evolution of Bovine Pancreatic Trypsin Inhibitor" Cold Spring Harbor Symp Quant Biol 52:511–519 (1987).

Cronlund et al., "A Low Molecular Weight Platelet Inhibitor of Factor Xia: Purification, Characterization, and Possible Role in Blood Coagulation" Biochemistry 31:1685–1694 (1992).

Davie et al., "The Coagulation Cascade: Initiation, Maintenance, and Regulation" Biochemistry 30(43):10363–10370 (1991).

De Maeyer, M. et al., "Recombinant Kunitz Inhibitors of Coagulation Proteases. II. Random Mutagenesis" Thrombosis and Haemostasis (abstract 1245) 69(6):888 (1993).

Dennis et al., "Kunitz Domain Inhibitors of Tissue Factor–Factor VIIa; I. Potent Inhibitors Selected from Libraries by Phage Display" Journal of Biological Chemistry 269(35):22129–22136 (1994).

Dennis et al., "Kunitz Domain Inhibitors of Tissue Factor–Factor VIIa; II. Potent and Specific Inhibitors by Competitive Phage Selection" Journal of Biological Chemistry 269(35):22137–22144 (1994).

Eigenbrot, C. et al., "Structural Effects Induced by Mutagenesis Affected by Crystal Packaging Factors: The Structure of a 30–51 Disulfide Mutant of Basic Pancreatic Trypsin Inhibitor" Proteins: Structure, Function, and Genetics 14:75–87 (1992).

(List continued on next page.)

Primary Examiner—Robert A. Wax
Assistant Examiner—Kawai Lau
Attorney, Agent, or Firm—Jeffrey S. Kubinec

[57] ABSTRACT

Potent and specific serine protease inhibitors are provided that are capable of inhibiting plasma kallikrein. The inhibitors are provided in pharmaceutical compositions for the treatment of diseases and disorders where inhibition of plasma kallikrein in indicated.

4 Claims, 5 Drawing Sheets

OTHER PUBLICATIONS

Eigenbrot, C. et al., "Structural effects induced by removal of a disulfide-bridge: The X-ray structure of the C30A/C51A mutant of basic pancreatic trypsin inhibitor at 1.6 Angstrom" *Protein Engineering* 3(7):591–598 (1990).

Fritz et al., "Biochemistry and Applications of Aprotinin, the Kallikrein Inhibitor from Bovine Organs" *Arzneimittel-Forschung/Drug Research* 33:479–494 (1983).

Fuhrer, C. et al., "Aprotinin in cardiopulmonary bypass—effects on the Hageman factor (FXII)–Kallikrein system and blood loss" *Blood Coagulation and Fibrinolysis* 3:99–104 (1992).

Girard et al., "Functional significance of the Kunitz type inhibitory domains of lipoprotein-associated coagulation inhibitor" *Nature* 338:518–520 (1989).

Girard et al., "Inhibition of Factor VIIa–Tissue Factor Coagulation Activity by a Hybrid Protein" *Science* 248:1421–1424 (1990).

Greer, "Comparative Modeling Methods: Application to the Family of the Mammalian Serine Proteases" *Proteins: Struct. Funct. Genet.* 7:317–334 (1990).

Hamamoto et al., "Inhibitory Properties of Full-length and Truncated Recombinant Tissue Factor Pathway Inhibitor (TFPI)" *Journal of Biological Chemistry* 268(12):8704–8710 (1993).

Haskel et al., "Prevention of Arterial Reocclusion After Thrombolysis With Recombinant Lipoprotein-Associated Coagulation Inhibitor" *Circulation* 84:821–827 (1991).

Holst et al., "Antithrombotic Properties of a Truncated Recombinant Tissue Factor Pathway Inhibitor in an Experimental Venous Thrombosis Model" *Haemostasis* 23(Suppl. 1):112–117 (1993).

Hynes et al., "X-ray Crystal Structure of the Protease Inhibitor Domain of Alzheimer's Amyloid β-Protein Precursor" *Biochemistry* 29:10018–10022 (1990).

Katori, M. et al., "Evidence for the involvement of a plasma kallikrein-kinin system in the immediate hypotension produced by endotoxin in anaesthetized rats" *Br. J. Pharmacol.* 98:1383–1391 (1989).

Kido et al., "Protease-Specificity of Kunitz Inhibitor Domain of Alzheimer's Disease Amyloid Protein Precursor" *Biochem. & Biophys. Res. Comm.* 167(2):716–721 (1990).

Kitchens et al., "Factor XI: A Review of Its Biochemistry and Deficiency" *Sem. in Thrombosis and Hemostasis* 17(1):55–72 (1991).

Kossiakoff et al., "Molecular recognition in biological systems: From activation to inhibition" *Bio. Society Transactions* 21:614–618 (1993).

Laskowski et al., "Protein Inhibitors of Protinases" *Ann. Rev. Biochem.* 49:593–626 (1980).

Lawson et al., "Complex-dependent Inhibition of Factor VIIa by Antithrombin III and Heparin" *Journal of Biological Chemisry* 268(2):767–770 (1993).

Mann, Kenneth G., "Correspondence –Response" *Blood* 82:1680–1681 (1993).

Marks et al., "Mutants of Bovine Pancreatic Trypsin Inhibitor Lacking Cysteines 14 and 38 Can Fold Properly" *Science* 235:1370–1373 (1987).

McGrath et al., "The Sequence and Reactive Site of Ecotin" *Journal of Biological Chemistry* 266(10):6620–6625 (1991).

Nordfang et al., "The C-Terminus of Tissue Factor Pathway Inhibitor is Essential to Its Anticoagulant Activity" *Biochemistry* 30:10371–10376 (1991).

Patston et al., "Reactivity of α 1-Antitrypsin Mutants against Proteolytic Enzymes of the Kallikrein–Kinin, Complement, and Fibrinolytic Systems" *Journal of Biological Chemistry* 265(18):10786–10791 (1990).

Perona and Craik, "Structural basis of substrate specificity in the serine proteases" *Protein Science* 4:337–360 (1995).

Perona et al., "Crystal Structures of Rat Anionic Trypsin Complexed with the Protein Inhibitors APPI and BPTI" *J. Mol. Biol.* 230:919–933 (1993).

Petersen et al., "Characterization of Human Tissue Factor Pathway Inhibitor Variants Expressed in *Saccharomyces cerevisiae*" *Journal of Biological Chemistry* 268:13344 13351 (1993).

Rao et al., "Binding of Factor VIIa to Tissue Factor Permits Rapid Antithrombin III/Heparin Inhibition of Factor VIIa" *Blood* 81(10):2600–2607 (1993).

Roberts et al., "Directed evolution of a protein: Selection of potent neutrophil elastase inhibitors displayed on M13 fusion phage" *Proc. Natl. Acad. Sci. USA* 89:2429–2433 (1992).

Royston, D., "The serine antiprotease aprotinin (Trasylol™): a novel approach to reducing postoperative bleeding" *Blood Coagulation and Fibrinolysis* 1:55–69 (1990).

Royston, D., et al., "Effect of aprotinin on need for blood transfusion after repeat open-heart surgery" *Lancet* pp. 1289–1291 (Dec. 5, 1987).

Salvesen et al., "Proteinase Inhibitors: /141–Macroglobulins, Serpins, and Kunins" *Hemostasis and Thrombosis: Basic Principles and Clin. Practice,* Colman et al., 3rd edition pp. 241–258 (1994).

Schapira et al., "Protection by Recombinant α 1-Antitrypsin Ala 357 Arg 358 against Arterial Hypotension Induced by Factor XII Fragment" *J. Clin. Invest.* 80:582–585 (1987).

Schmaier et al., "Protease Nexin 2/Amyloid Beta Protein Precursor" *J. Clin. Invest.* 92:2540–2545 (1993).

Scott et al., "Alpha 1-antitrypsin-Pittsburgh: A Potent Inhibitor of Human Plasma Factor XIa, Kallikrein, and Factor XIIf" *J. Clin. Invest.* 77:631–634 (1986).

Scott et al., "Inactivation of Factor XIa by Plasma Protease Inhibitors" *J. Clin. Invest.* 69:844–852 (1982).

Scott et al., "Kinetics of Inhibition of Human Plasma Kallikrein by a Site Specific Modified Inhibitor Arg15 – Aprotinin: Evaluation Using a Microplate System and Comparison With Other Protease" *Blood* 69(5):1431–1436 (1987).

Sinha et al., "Conversion of the Alzheimer's β-Amyloid Precursor Protein (APP) Kunitz Domain into a Potent Human Neutrophil Elastase Inhibitor" *Journal of Biological Chemistry* 266(31):21011–21013 (1991).

Smith et al., "Platelet Coagulation Factor Xia–Inhibitor, a Form of Alzheimer Amyloid Precursor Protein" *Science* 248:1126–1128 (1990).

Thiele et al., "Gene Synthesis, Expression and Isolation of an Inhibitorily Active MS–2 pol Stefin B Fusion Protein and Preparation of Des [Met1,2/2]stefin B" *Biol. Chem. Hoppe Seyler* 369:1167–1178 (1988).

Van Den Besselaar et al., "Tissue Factor–Induced Coagulation Can Be Inhibited by Aprotinin (Trasylol)" *Thrombosis and Haemostasis* 69:298–299 (1993).

Van Nostrand et al., "Immunopurification and Protease Inhibitory Properties of Protease Nexin–2/Amyloid Beta–Protein Precursor" *Journal of Biological Chemistry* 265(17):9591–9594 (1990).

Velz et al., "The domain structure of the inhibitor subunit of human inter-α trypsin inhibitor reflects the exon structure of its gene" *FEBS* 06902 Letter 245(1,2):137–140 (1989).

Wachtfogel et al., "Aprotinin inhibits the contact, neutrophil, and platelet activation systems during simulated extracorporeal perfusion" *J. Thoracic and Cardiovascular Surgery* 106(1):1–10 (1993).

Wagner et al., "High Level Expression, Purification, and Characterization of the Kunitz-Type Protease Inhibitor Domain of Protease Nexin-2/Amyloid Beta-Protein Precursor" *Biochem. & Biophys. Res. Comm.* 186:1138–1145 (1992).

Westaby, S., "Aprotinin in Perspective" *Ann. Thorac. Surg.* 55:1033–1041 (1993).

FIG. 2

SEQUENCE LISTING ( 1 ) GENERAL INFORMATION:

( i i i ) NUMBER OF SEQUENCES: 72

( 2 ) INFORMATION FOR SEQ ID NO:1:

( i ) SEQUENCE CHARACTERISTICS:
      ( A ) LENGTH: 58 amino acids
      ( B ) TYPE: Amino Acid
      ( D ) TOPOLOGY: Linear ( x i ) SEQUENCE DESCRIPTION: SEQ ID NO:1:

```
Val Arg Glu Val Cys Ser Glu Gln Ala Glu Ser Gly His Cys Arg
  1               5                  10                  15

Ala Ala Ile Pro Arg Trp Tyr Phe Asp Val Thr Glu Gly Lys Cys
                 20                  25                  30

Ala Pro Phe Phe Tyr Gly Gly Cys Gly Gly Asn Arg Asn Asn Phe
                 35                  40                  45

Asp Thr Glu Glu Tyr Cys Ala Ala Val Cys Gly Ser Ala
                 50                  55          58
```

( 2 ) INFORMATION FOR SEQ ID NO:2:

( i ) SEQUENCE CHARACTERISTICS:
      ( A ) LENGTH: 58 amino acids
      ( B ) TYPE: Amino Acid
      ( D ) TOPOLOGY: Linear ( x i ) SEQUENCE DESCRIPTION: SEQ ID NO:2:

```
Val Arg Glu Val Cys Ser Glu Gln Ala Glu Thr Gly His Cys Arg
  1               5                  10                  15

Ala Ala Ile Pro Arg Trp Tyr Phe Asp Val Thr Glu Gly Lys Cys
                 20                  25                  30

Ala Pro Phe Phe Tyr Gly Gly Cys Gly Gly Asn Arg Asn Asn Phe
                 35                  40                  45

Asp Thr Glu Glu Tyr Cys Ala Ala Val Cys Gly Ser Ala
                 50                  55          58
```

( 2 ) INFORMATION FOR SEQ ID NO:3:

( i ) SEQUENCE CHARACTERISTICS:
      ( A ) LENGTH: 58 amino acids
      ( B ) TYPE: Amino Acid
      ( D ) TOPOLOGY: Linear ( x i ) SEQUENCE DESCRIPTION: SEQ ID NO:3:

```
Val Arg Glu Val Cys Ser Glu Gln Ala Glu Leu Gly His Cys Arg
  1               5                  10                  15

Ala Ala Ile Pro Arg Trp Tyr Phe Asp Val Thr Glu Gly Lys Cys
                 20                  25                  30

Ala Pro Phe Phe Tyr Gly Gly Cys Gly Gly Asn Arg Asn Asn Phe
                 35                  40                  45

Asp Thr Glu Glu Tyr Cys Ala Ala Val Cys Gly Ser Ala
                 50                  55          58
```

( 2 ) INFORMATION FOR SEQ ID NO:4:

( i ) SEQUENCE CHARACTERISTICS:
      ( A ) LENGTH: 58 amino acids
      ( B ) TYPE: Amino Acid
      ( D ) TOPOLOGY: Linear (xi) SEQUENCE DESCRIPTION: SEQ ID NO:4:

| Val | Arg | Glu | Val | Cys | Ser | Gln | Ala | Glu | Asp | Gly | Pro | Cys | Arg |
| 1 | | | | 5 | | | | 10 | | | | | 15 |

| Ala | Ala | Ile | Pro | Arg | Trp | Tyr | Phe | Asp | Val | Thr | Glu | Gly | Lys | Cys |
| | | | | 20 | | | | | 25 | | | | | 30 |

| Ala | Pro | Phe | Phe | Tyr | Gly | Gly | Cys | Gly | Gly | Asn | Arg | Asn | Asn | Phe |
| | | | | 35 | | | | | 40 | | | | | 45 |

| Asp | Thr | Glu | Glu | Tyr | Cys | Ala | Ala | Val | Cys | Gly | Ser | Ala |
| | | | | 50 | | | | | 55 | | | 58 |

(2) INFORMATION FOR SEQ ID NO:5:

(i) SEQUENCE CHARACTERISTICS:
        (A) LENGTH: 58 amino acids
        (B) TYPE: Amino Acid
        (D) TOPOLOGY: Linear (xi) SEQUENCE DESCRIPTION: SEQ ID NO:5:

| Val | Arg | Glu | Val | Cys | Ser | Gln | Ala | Glu | Glu | Gly | His | Cys | Arg |
| 1 | | | | 5 | | | | 10 | | | | | 15 |

| Ala | Ala | Ile | Leu | Arg | Trp | Tyr | Phe | Asp | Val | Thr | Glu | Gly | Lys | Cys |
| | | | | 20 | | | | | 25 | | | | | 30 |

| Ala | Pro | Phe | Phe | Tyr | Gly | Gly | Cys | Gly | Gly | Asn | Arg | Asn | Asn | Phe |
| | | | | 35 | | | | | 40 | | | | | 45 |

| Asp | Thr | Glu | Glu | Tyr | Cys | Ala | Ala | Val | Cys | Gly | Ser | Ala |
| | | | | 50 | | | | | 55 | | | 58 |

(2) INFORMATION FOR SEQ ID NO:6:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO:6:

| Val | Arg | Glu | Val | Cys | Ser | Gln | Ala | Glu | Glu |
| 1 | | | | 5 | | | | | 10 |

(2) INFORMATION FOR SEQ ID NO:7:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO:7:

| Met | His | Ser | Phe | Cys | Ala | Phe | Lys | Ala | Asp |
| 1 | | | | 5 | | | | | 10 |

(2) INFORMATION FOR SEQ ID NO:8:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO:8:

| Lys | Pro | Asp | Phe | Cys | Phe | Leu | Glu | Glu | Asp |
| 1 | | | | 5 | | | | | 10 |

(2) INFORMATION FOR SEQ ID NO:9:

(i) SEQUENCE CHARACTERISTICS:

( A ) LENGTH: 10 amino acids
             ( B ) TYPE: Amino Acid
             ( D ) TOPOLOGY: Linear ( x i ) SEQUENCE DESCRIPTION: SEQ ID NO:9:

Gly Pro Ser Trp Cys Leu Thr Pro Ala Asp
 1           5                    10

( 2 ) INFORMATION FOR SEQ ID NO:10:

( i ) SEQUENCE CHARACTERISTICS:
             ( A ) LENGTH: 10 amino acids
             ( B ) TYPE: Amino Acid
             ( D ) TOPOLOGY: Linear ( x i ) SEQUENCE DESCRIPTION: SEQ ID NO:10:

Lys Glu Asp Ser Cys Gln Leu Gly Tyr Ser
 1           5                    10

( 2 ) INFORMATION FOR SEQ ID NO:11:

( i ) SEQUENCE CHARACTERISTICS:
             ( A ) LENGTH: 10 amino acids
             ( B ) TYPE: Amino Acid
             ( D ) TOPOLOGY: Linear ( x i ) SEQUENCE DESCRIPTION: SEQ ID NO:11:

Thr Val Ala Ala Cys Asn Leu Pro Ile Val
 1           5                    10

( 2 ) INFORMATION FOR SEQ ID NO:12:

( i ) SEQUENCE CHARACTERISTICS:
             ( A ) LENGTH: 10 amino acids
             ( B ) TYPE: Amino Acid
             ( D ) TOPOLOGY: Linear ( x i ) SEQUENCE DESCRIPTION: SEQ ID NO:12:

Leu Pro Asn Val Cys Ala Phe Pro Met Glu
 1           5                    10

( 2 ) INFORMATION FOR SEQ ID NO:13:

( i ) SEQUENCE CHARACTERISTICS:
             ( A ) LENGTH: 10 amino acids
             ( B ) TYPE: Amino Acid
             ( D ) TOPOLOGY: Linear ( x i ) SEQUENCE DESCRIPTION: SEQ ID NO:13:

Arg Pro Asp Phe Cys Leu Glu Pro Pro Tyr
 1           5                    10

( 2 ) INFORMATION FOR SEQ ID NO:14:

( i ) SEQUENCE CHARACTERISTICS:
             ( A ) LENGTH: 14 amino acids
             ( B ) TYPE: Amino Acid
             ( D ) TOPOLOGY: Linear ( x i ) SEQUENCE DESCRIPTION: SEQ ID NO:14:

Arg Trp Tyr Phe Asp Val Thr Glu Gly Lys Cys Ala Pro Phe
 1           5                    10                  14

( 2 ) INFORMATION FOR SEQ ID NO:15:

( i ) SEQUENCE CHARACTERISTICS:
             ( A ) LENGTH: 14 amino acids
             ( B ) TYPE: Amino Acid ( D ) TOPOLOGY: Linear ( x i ) SEQUENCE DESCRIPTION: SEQ ID NO:15:

Arg Phe Phe Phe Asn Ile Phe Thr Arg Gln Cys Glu Glu Phe
1               5                   10                  14

( 2 ) INFORMATION FOR SEQ ID NO:16:

( i ) SEQUENCE CHARACTERISTICS:
      ( A ) LENGTH: 14 amino acids
      ( B ) TYPE: Amino Acid
      ( D ) TOPOLOGY: Linear ( x i ) SEQUENCE DESCRIPTION: SEQ ID NO:16:

Arg Tyr Phe Tyr Asn Asn Gln Thr Lys Gln Cys Glu Arg Phe
1               5                   10                  14

( 2 ) INFORMATION FOR SEQ ID NO:17:

( i ) SEQUENCE CHARACTERISTICS:
      ( A ) LENGTH: 14 amino acids
      ( B ) TYPE: Amino Acid
      ( D ) TOPOLOGY: Linear ( x i ) SEQUENCE DESCRIPTION: SEQ ID NO:17:

Arg Phe Tyr Tyr Asn Ser Val Ile Gly Lys Cys Arg Pro Phe
1               5                   10                  14

( 2 ) INFORMATION FOR SEQ ID NO:18:

( i ) SEQUENCE CHARACTERISTICS:
      ( A ) LENGTH: 14 amino acids
      ( B ) TYPE: Amino Acid
      ( D ) TOPOLOGY: Linear ( x i ) SEQUENCE DESCRIPTION: SEQ ID NO:18:

Arg Tyr Phe Tyr Asn Gly Thr Ser Met Ala Cys Glu Thr Phe
1               5                   10                  14

( 2 ) INFORMATION FOR SEQ ID NO:19:

( i ) SEQUENCE CHARACTERISTICS:
      ( A ) LENGTH: 14 amino acids
      ( B ) TYPE: Amino Acid
      ( D ) TOPOLOGY: Linear ( x i ) SEQUENCE DESCRIPTION: SEQ ID NO:19:

Leu Trp Ala Phe Asp Ala Val Lys Gly Lys Cys Val Leu Phe
1               5                   10                  14

( 2 ) INFORMATION FOR SEQ ID NO:20:

( i ) SEQUENCE CHARACTERISTICS:
      ( A ) LENGTH: 14 amino acids
      ( B ) TYPE: Amino Acid
      ( D ) TOPOLOGY: Linear ( x i ) SEQUENCE DESCRIPTION: SEQ ID NO:20:

Lys Trp Tyr Tyr Asp Pro Asn Thr Lys Ser Cys Ala Arg Phe
1               5                   10                  14

( 2 ) INFORMATION FOR SEQ ID NO:21:

( i ) SEQUENCE CHARACTERISTICS:
      ( A ) LENGTH: 14 amino acids
      ( B ) TYPE: Amino Acid
      ( D ) TOPOLOGY: Linear ( x i ) SEQUENCE DESCRIPTION: SEQ ID NO:21:

Arg Trp Phe Phe Asn Phe Glu Thr Gly Glu Cys Glu Leu Phe
1               5                   10                  14

( 2 ) INFORMATION FOR SEQ ID NO:22:

( i ) SEQUENCE CHARACTERISTICS:
        ( A ) LENGTH: 14 amino acids
        ( B ) TYPE: Amino Acid
        ( D ) TOPOLOGY: Linear ( x i ) SEQUENCE DESCRIPTION: SEQ ID NO:22:

Arg Tyr Phe Tyr Asn Ala Lys Ala Gly Leu Cys Gln Thr Phe
1               5                   10                  14

( 2 ) INFORMATION FOR SEQ ID NO:23:

( i ) SEQUENCE CHARACTERISTICS:
        ( A ) LENGTH: 24 amino acids
        ( B ) TYPE: Amino Acid
        ( D ) TOPOLOGY: Linear ( x i ) SEQUENCE DESCRIPTION: SEQ ID NO:23:

Tyr Gly Gly Cys Gly Gly Asn Arg Asn Asn Phe Asp Thr Glu Glu
1               5                   10                      15

Tyr Cys Ala Ala Val Cys Gly Ser Ala
                20              24

( 2 ) INFORMATION FOR SEQ ID NO:24:

( i ) SEQUENCE CHARACTERISTICS:
        ( A ) LENGTH: 24 amino acids
        ( B ) TYPE: Amino Acid
        ( D ) TOPOLOGY: Linear ( x i ) SEQUENCE DESCRIPTION: SEQ ID NO:24:

Tyr Gly Gly Cys Gly Gly Asn Arg Asn Asn Phe Asp Thr Glu Glu
1               5                   10                      15

Tyr Cys Met Ala Val Cys Gly Ser Ala
                20              24

( 2 ) INFORMATION FOR SEQ ID NO:25:

( i ) SEQUENCE CHARACTERISTICS:
        ( A ) LENGTH: 24 amino acids
        ( B ) TYPE: Amino Acid
        ( D ) TOPOLOGY: Linear ( x i ) SEQUENCE DESCRIPTION: SEQ ID NO:25:

Tyr Gly Gly Cys Glu Gly Asn Gln Asn Arg Phe Glu Ser Leu Glu
1               5                   10                      15

Glu Cys Lys Lys Met Cys Thr Arg Asp
                20              24

( 2 ) INFORMATION FOR SEQ ID NO:26:

( i ) SEQUENCE CHARACTERISTICS:
        ( A ) LENGTH: 24 amino acids
        ( B ) TYPE: Amino Acid
        ( D ) TOPOLOGY: Linear ( x i ) SEQUENCE DESCRIPTION: SEQ ID NO:26:

Tyr Gly Gly Cys Leu Gly Asn Met Asn Asn Phe Glu Thr Leu Glu
1               5                   10                      15

Glu Cys Lys Asn Ile Cys Glu Asp Gly 20                    24

( 2 ) INFORMATION FOR SEQ ID NO:27:

( i ) SEQUENCE CHARACTERISTICS:
        ( A ) LENGTH: 24 amino acids
        ( B ) TYPE: Amino Acid
        ( D ) TOPOLOGY: Linear ( x i ) SEQUENCE DESCRIPTION: SEQ ID NO:27:

Tyr Ser Gly Cys Gly Gly Asn Glu Asn Asn Phe Thr Ser Lys Gln
1               5                   10                  15

Glu Cys Leu Arg Ala Cys Lys Lys Gly
                20              24

( 2 ) INFORMATION FOR SEQ ID NO:28:

( i ) SEQUENCE CHARACTERISTICS:
        ( A ) LENGTH: 24 amino acids
        ( B ) TYPE: Amino Acid
        ( D ) TOPOLOGY: Linear ( x i ) SEQUENCE DESCRIPTION: SEQ ID NO:28:

Tyr Gly Gly Cys Met Gly Asn Gly Asn Asn Phe Val Thr Glu Lys
1               5                   10                  15

Glu Cys Leu Gln Thr Cys Arg Thr Val
                20              24

( 2 ) INFORMATION FOR SEQ ID NO:29:

( i ) SEQUENCE CHARACTERISTICS:
        ( A ) LENGTH: 24 amino acids
        ( B ) TYPE: Amino Acid
        ( D ) TOPOLOGY: Linear ( x i ) SEQUENCE DESCRIPTION: SEQ ID NO:29:

Tyr Gly Gly Cys Gln Gly Asn Gly Asn Lys Phe Tyr Ser Glu Lys
1               5                   10                  15

Glu Cys Arg Glu Tyr Cys Gly Val Pro
                20              24

( 2 ) INFORMATION FOR SEQ ID NO:30:

( i ) SEQUENCE CHARACTERISTICS:
        ( A ) LENGTH: 24 amino acids
        ( B ) TYPE: Amino Acid
        ( D ) TOPOLOGY: Linear ( x i ) SEQUENCE DESCRIPTION: SEQ ID NO:30:

Tyr Gly Gly Cys Gly Gly Asn Glu Asn Lys Phe Gly Ser Gln Lys
1               5                   10                  15

Glu Cys Glu Lys Val Cys Ala Pro Val
                20              24

( 2 ) INFORMATION FOR SEQ ID NO:31:

( i ) SEQUENCE CHARACTERISTICS:
        ( A ) LENGTH: 24 amino acids
        ( B ) TYPE: Amino Acid
        ( D ) TOPOLOGY: Linear ( x i ) SEQUENCE DESCRIPTION: SEQ ID NO:31:

Tyr Gly Gly Cys Gly Gly Asn Ser Asn Asn Phe Leu Arg Lys Glu
1               5                   10                  15

Lys Cys Glu Lys Phe Cys Lys Phe Thr ( 2 ) INFORMATION FOR SEQ ID NO:32:

( i ) SEQUENCE CHARACTERISTICS:
    ( A ) LENGTH: 24 amino acids
    ( B ) TYPE: Amino Acid
    ( D ) TOPOLOGY: Linear ( x i ) SEQUENCE DESCRIPTION: SEQ ID NO:32:

```
Tyr  Gly  Gly  Cys  Arg  Ala  Lys  Arg  Asn  Asn  Phe  Lys  Ser  Ala  Glu
 1                   5                        10                       15

Asp  Cys  Met  Arg  Thr  Cys  Gly  Gly  Ala
                    20                   24
```

( 2 ) INFORMATION FOR SEQ ID NO:33:

( i ) SEQUENCE CHARACTERISTICS:
    ( A ) LENGTH: 58 amino acids
    ( B ) TYPE: Amino Acid
    ( D ) TOPOLOGY: Linear ( x i ) SEQUENCE DESCRIPTION: SEQ ID NO:33:

```
Val  Arg  Glu  Val  Cys  Ser  Glu  Gln  Ala  Glu  Gly  Arg  Cys  Arg
 1                   5                        10                  15

Ala  Ser  Ile  Leu  Arg  Trp  Tyr  Phe  Asp  Val  Thr  Glu  Gly  Lys  Cys
                    20                        25                       30

Ala  Pro  Phe  Phe  Tyr  Gly  Gly  Cys  Gly  Gly  Asn  Arg  Asn  Asn  Phe
                    35                        40                       45

Asp  Thr  Glu  Glu  Tyr  Cys  Ala  Ala  Val  Cys  Gly  Ser  Ala
                    50                        55            58
```

( 2 ) INFORMATION FOR SEQ ID NO:34:

( i ) SEQUENCE CHARACTERISTICS:
    ( A ) LENGTH: 58 amino acids
    ( B ) TYPE: Amino Acid
    ( D ) TOPOLOGY: Linear ( x i ) SEQUENCE DESCRIPTION: SEQ ID NO:34:

```
Val  Arg  Glu  Val  Cys  Ser  Glu  Gln  Ala  Glu  Thr  Gly  Pro  Cys  Arg
 1                   5                        10                       15

Ala  Met  Ile  Ser  Arg  Trp  Tyr  Phe  Asp  Val  Thr  Glu  Gly  Lys  Cys
                    20                        25                       30

Ala  Pro  Phe  Phe  Tyr  Gly  Gly  Cys  Gly  Gly  Asn  Arg  Asn  Asn  Phe
                    35                        40                       45

Asp  Thr  Glu  Glu  Tyr  Cys  Met  Ala  Val  Cys  Gly  Ser  Ala
                    50                        55            58
```

( 2 ) INFORMATION FOR SEQ ID NO:35:

( i ) SEQUENCE CHARACTERISTICS:
    ( A ) LENGTH: 58 amino acids
    ( B ) TYPE: Amino Acid
    ( D ) TOPOLOGY: Linear ( x i ) SEQUENCE DESCRIPTION: SEQ ID NO:35:

```
Met  His  Ser  Phe  Cys  Ala  Phe  Lys  Ala  Asp  Asp  Gly  Pro  Cys  Lys
 1                   5                        10                       15

Ala  Ile  Met  Lys  Arg  Phe  Phe  Phe  Asn  Ile  Phe  Thr  Arg  Gln  Cys
                    20                        25                       30

Glu  Glu  Phe  Ile  Tyr  Gly  Gly  Cys  Glu  Gly  Asn  Gln  Asn  Arg  Phe
                    35                        40                       45
```

```
Glu  Ser  Leu  Glu  Glu  Cys  Lys  Lys  Met  Cys  Thr  Arg  Asp
                    50                  55             58
```

( 2 ) INFORMATION FOR SEQ ID NO:36:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:36:

```
Lys  Pro  Asp  Phe  Cys  Phe  Leu  Glu  Glu  Asp  Pro  Gly  Ile  Cys  Arg
 1                   5                        10                       15

Gly  Tyr  Ile  Thr  Arg  Tyr  Phe  Tyr  Asn  Asn  Gln  Thr  Lys  Gln  Cys
                    20                       25                       30

Glu  Arg  Phe  Lys  Tyr  Gly  Gly  Cys  Leu  Gly  Asn  Met  Asn  Asn  Phe
                    35                       40                       45

Glu  Thr  Leu  Glu  Glu  Cys  Lys  Asn  Ile  Cys  Glu  Asp  Gly
                    50                       55             58
```

( 2 ) INFORMATION FOR SEQ ID NO:37:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:37:

```
Gly  Pro  Ser  Trp  Cys  Leu  Thr  Pro  Ala  Asp  Arg  Gly  Leu  Cys  Arg
 1                   5                        10                       15

Ala  Asn  Glu  Asn  Arg  Phe  Tyr  Tyr  Asn  Ser  Val  Ile  Gly  Lys  Cys
                    20                       25                       30

Arg  Pro  Phe  Lys  Tyr  Ser  Gly  Cys  Gly  Gly  Asn  Glu  Asn  Asn  Phe
                    35                       40                       45

Thr  Ser  Lys  Gln  Glu  Cys  Leu  Arg  Ala  Cys  Lys  Lys  Gly
                    50                       55             58
```

( 2 ) INFORMATION FOR SEQ ID NO:38:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:38:

```
Lys  Glu  Asp  Ser  Cys  Gln  Leu  Gly  Tyr  Ser  Ala  Gly  Pro  Cys  Met
 1                   5                        10                       15

Gly  Met  Thr  Ser  Arg  Tyr  Phe  Tyr  Asn  Gly  Thr  Ser  Met  Ala  Cys
                    20                       25                       30

Glu  Thr  Phe  Gln  Tyr  Gly  Gly  Cys  Met  Gly  Asn  Gly  Asn  Asn  Phe
                    35                       40                       45

Val  Thr  Glu  Lys  Glu  Cys  Leu  Gln  Thr  Cys  Arg  Thr  Val
                    50                       55             58
```

( 2 ) INFORMATION FOR SEQ ID NO:39:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:39:

```
Thr Val Ala Ala Cys Asn Leu Pro Ile Val Arg Gly Pro Cys Arg
 1           5                   10                      15

Ala Phe Ile Gln Leu Trp Ala Phe Asp Ala Val Lys Gly Lys Cys
                 20                  25                   30

Val Leu Phe Pro Tyr Gly Gly Cys Gln Gly Asn Gly Asn Lys Phe
                 35              40                       45

Tyr Ser Glu Lys Glu Cys Arg Glu Tyr Cys Gly Val Pro
                 50              55          58
```

( 2 ) INFORMATION FOR SEQ ID NO:40:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:40:

```
Glu Thr Asp Ile Cys Lys Leu Pro Lys Asp Glu Gly Thr Cys Arg
 1           5                   10                      15

Asp Phe Ile Leu Lys Trp Tyr Tyr Asp Pro Asn Thr Lys Ser Cys
                 20                  25                   30

Ala Arg Phe Trp Tyr Gly Gly Cys Gly Gly Asn Glu Asn Lys Phe
                 35              40                       45

Gly Ser Gln Lys Glu Cys Glu Lys Val Cys Ala Pro Val
                 50              55          58
```

( 2 ) INFORMATION FOR SEQ ID NO:41:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:41:

```
Leu Pro Asn Val Cys Ala Phe Pro Met Glu Lys Gly Pro Cys Gln
 1           5                   10                      15

Thr Tyr Met Thr Arg Trp Phe Phe Asn Phe Glu Thr Gly Glu Cys
                 20                  25                   30

Glu Leu Phe Ala Tyr Gly Gly Cys Gly Gly Asn Ser Asn Asn Phe
                 35              40                       45

Leu Arg Lys Glu Lys Cys Glu Lys Phe Cys Lys Phe Thr
                 50              55          58
```

( 2 ) INFORMATION FOR SEQ ID NO:42:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:42:

```
Arg Pro Asp Phe Cys Leu Glu Pro Pro Tyr Thr Gly Pro Cys Lys
 1           5                   10                      15

Ala Arg Ile Ile Arg Tyr Phe Tyr Asn Ala Lys Ala Gly Leu Cys
                 20                  25                   30

Gln Thr Phe Val Tyr Gly Gly Cys Arg Ala Lys Arg Asn Asn Phe
                 35              40                       45

Lys Ser Ala Glu Asp Cys Met Arg Thr Cys Gly Gly Ala
                 50              55          58
```

( 2 ) INFORMATION FOR SEQ ID NO:43:

( i ) SEQUENCE CHARACTERISTICS:
   ( A ) LENGTH: 58 amino acids
   ( B ) TYPE: Amino Acid
   ( D ) TOPOLOGY: Linear ( x i ) SEQUENCE DESCRIPTION: SEQ ID NO:43:

| Val | Arg | Glu | Val | Cys | Ser | Gln | Ala | Glu | Thr | Gly | Pro | Cys | Arg |
| 1 | | | | 5 | | | | 10 | | | | | 15 |

| Ala | Leu | His | Ser | Arg | Trp | Tyr | Phe | Asp | Val | Thr | Glu | Gly | Lys | Cys |
| | | | | 20 | | | | 25 | | | | | 30 |

| Ala | Pro | Phe | Tyr | Tyr | Gly | Gly | Cys | Gly | Gly | Asn | Arg | Asn | Asn | Phe |
| | | | | 35 | | | | 40 | | | | | 45 |

| Asp | Thr | Glu | Glu | Tyr | Cys | Ala | Ala | Val | Cys | Gly | Ser | Ala |
| | | | | 50 | | | | 55 | | | 58 |

( 2 ) INFORMATION FOR SEQ ID NO:44:

( i ) SEQUENCE CHARACTERISTICS:
   ( A ) LENGTH: 58 amino acids
   ( B ) TYPE: Amino Acid
   ( D ) TOPOLOGY: Linear ( x i ) SEQUENCE DESCRIPTION: SEQ ID NO:44:

| Val | Arg | Glu | Val | Cys | Ser | Gln | Ala | Glu | Thr | Gly | Pro | Cys | Arg |
| 1 | | | | 5 | | | | 10 | | | | | 15 |

| Ala | Ala | His | Ser | Arg | Trp | Tyr | Phe | Asp | Val | Thr | Glu | Gly | Lys | Cys |
| | | | | 20 | | | | 25 | | | | | 30 |

| Ala | Pro | Phe | Val | Tyr | Gly | Gly | Cys | Gly | Gly | Asn | Arg | Asn | Asn | Phe |
| | | | | 35 | | | | 40 | | | | | 45 |

| Asp | Thr | Glu | Glu | Tyr | Cys | Ala | Ala | Val | Cys | Gly | Ser | Ala |
| | | | | 50 | | | | 55 | | | 58 |

( 2 ) INFORMATION FOR SEQ ID NO:45:

( i ) SEQUENCE CHARACTERISTICS:
   ( A ) LENGTH: 58 amino acids
   ( B ) TYPE: Amino Acid
   ( D ) TOPOLOGY: Linear ( x i ) SEQUENCE DESCRIPTION: SEQ ID NO:45:

| Val | Arg | Glu | Val | Cys | Ser | Gln | Ala | Glu | Asp | Gly | His | Cys | Arg |
| 1 | | | | 5 | | | | 10 | | | | | 15 |

| Ala | Ala | His | Pro | Arg | Trp | Tyr | Phe | Asp | Val | Thr | Glu | Gly | Lys | Cys |
| | | | | 20 | | | | 25 | | | | | 30 |

| Ala | Pro | Phe | Phe | Tyr | Gly | Gly | Cys | Gly | Gly | Asn | Arg | Asn | Asn | Phe |
| | | | | 35 | | | | 40 | | | | | 45 |

| Asp | Thr | Glu | Glu | Tyr | Cys | Ala | Ala | Val | Cys | Gly | Ser | Ala |
| | | | | 50 | | | | 55 | | | 58 |

( 2 ) INFORMATION FOR SEQ ID NO:46:

( i ) SEQUENCE CHARACTERISTICS:
   ( A ) LENGTH: 58 amino acids
   ( B ) TYPE: Amino Acid
   ( D ) TOPOLOGY: Linear ( x i ) SEQUENCE DESCRIPTION: SEQ ID NO:46:

| Val | Arg | Glu | Val | Cys | Ser | Gln | Ala | Glu | Asp | Gly | His | Cys | Arg |
| 1 | | | | 5 | | | | 10 | | | | | 15 |

| Ala | Ala | His | Pro | Arg | Trp | Tyr | Phe | Asp | Val | Thr | Glu | Gly | Lys | Cys |
| | | | | 20 | | | | 25 | | | | | 30 |

```
Ala Pro Phe Val Tyr Gly Gly Cys Gly Gly Asn Arg Asn Asn Phe
             35                   40                      45

Asp Thr Glu Glu Tyr Cys Ala Ala Val Cys Gly Ser Ala
             50                  55          58
```

( 2 ) INFORMATION FOR SEQ ID NO:47:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:47:

```
Val Arg Glu Val Cys Ser Glu Gln Ala Glu Asp Gly His Cys Arg
 1               5                   10                   15

Ala Ala His Pro Arg Trp Tyr Phe Asp Val Thr Glu Gly Lys Cys
             20                  25                      30

Ala Pro Phe Tyr Tyr Gly Gly Cys Gly Gly Asn Arg Asn Asn Phe
             35                  40                      45

Asp Thr Glu Glu Tyr Cys Ala Ala Val Cys Gly Ser Ala
             50                  55          58
```

( 2 ) INFORMATION FOR SEQ ID NO:48:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:48:

```
Val Arg Glu Val Cys Ser Glu Gln Ala Glu Pro Gly His Cys Arg
 1               5                   10                   15

Ala Ala His Pro Arg Trp Tyr Phe Asp Val Thr Glu Gly Lys Cys
             20                  25                      30

Ala Pro Phe Phe Tyr Gly Gly Cys Gly Gly Asn Arg Asn Asn Phe
             35                  40                      45

Asp Thr Glu Glu Tyr Cys Ala Ala Val Cys Gly Ser Ala
             50                  55          58
```

( 2 ) INFORMATION FOR SEQ ID NO:49:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:49:

```
Val Arg Glu Val Cys Ser Glu Gln Ala Glu Pro Gly His Cys Arg
 1               5                   10                   15

Ala Ala His Pro Arg Trp Tyr Phe Asp Val Thr Glu Gly Lys Cys
             20                  25                      30

Ala Pro Phe Val Tyr Gly Gly Cys Gly Gly Asn Arg Asn Asn Phe
             35                  40                      45

Asp Thr Glu Glu Tyr Cys Ala Ala Val Cys Gly Ser Ala
             50                  55          58
```

( 2 ) INFORMATION FOR SEQ ID NO:50:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:50:

| Val | Arg | Glu | Val | Cys | Ser | Glu | Gln | Ala | Glu | Pro | Gly | His | Cys | Arg |
| 1 | | | | 5 | | | | | 10 | | | | | 15 |

| Ala | Ala | His | Pro | Arg | Trp | Tyr | Phe | Asp | Val | Thr | Glu | Gly | Lys | Cys |
| | | | | 20 | | | | | 25 | | | | | 30 |

| Ala | Pro | Phe | Tyr | Tyr | Gly | Gly | Cys | Gly | Gly | Asn | Arg | Asn | Asn | Phe |
| | | | | 35 | | | | | 40 | | | | | 45 |

| Asp | Thr | Glu | Glu | Tyr | Cys | Ala | Ala | Val | Cys | Gly | Ser | Ala |
| | | | | 50 | | | | | 55 | | | 58 |

( 2 ) INFORMATION FOR SEQ ID NO:51:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:51:

| Val | Arg | Glu | Val | Cys | Ser | Glu | Gln | Ala | Glu | Glu | Gly | His | Cys | Arg |
| 1 | | | | 5 | | | | | 10 | | | | | 15 |

| Ala | Ala | His | Pro | Arg | Trp | Tyr | Phe | Asp | Val | Thr | Glu | Gly | Lys | Cys |
| | | | | 20 | | | | | 25 | | | | | 30 |

| Ala | Pro | Phe | Phe | Tyr | Gly | Gly | Cys | Gly | Gly | Asn | Arg | Asn | Asn | Phe |
| | | | | 35 | | | | | 40 | | | | | 45 |

| Asp | Thr | Glu | Glu | Tyr | Cys | Ala | Ala | Val | Cys | Gly | Ser | Ala |
| | | | | 50 | | | | | 55 | | | 58 |

( 2 ) INFORMATION FOR SEQ ID NO:52:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:52:

| Val | Arg | Glu | Val | Cys | Ser | Glu | Gln | Ala | Glu | Glu | Gly | His | Cys | Arg |
| 1 | | | | 5 | | | | | 10 | | | | | 15 |

| Ala | Ala | His | Pro | Arg | Trp | Tyr | Phe | Asp | Val | Thr | Glu | Gly | Lys | Cys |
| | | | | 20 | | | | | 25 | | | | | 30 |

| Ala | Pro | Phe | Val | Tyr | Gly | Gly | Cys | Gly | Gly | Asn | Arg | Asn | Asn | Phe |
| | | | | 35 | | | | | 40 | | | | | 45 |

| Asp | Thr | Glu | Glu | Tyr | Cys | Ala | Ala | Val | Cys | Gly | Ser | Ala |
| | | | | 50 | | | | | 55 | | | 58 |

( 2 ) INFORMATION FOR SEQ ID NO:53:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:53:

| Val | Arg | Glu | Val | Cys | Ser | Glu | Gln | Ala | Glu | Glu | Gly | His | Cys | Arg |
| 1 | | | | 5 | | | | | 10 | | | | | 15 |

| Ala | Ala | His | Pro | Arg | Trp | Tyr | Phe | Asp | Val | Thr | Glu | Gly | Lys | Cys |
| | | | | 20 | | | | | 25 | | | | | 30 |

| Ala | Pro | Phe | Tyr | Tyr | Gly | Gly | Cys | Gly | Gly | Asn | Arg | Asn | Asn | Phe |
| | | | | 35 | | | | | 40 | | | | | 45 |

| Asp | Thr | Glu | Glu | Tyr | Cys | Ala | Ala | Val | Cys | Gly | Ser | Ala |
| | | | | 50 | | | | | 55 | | | 58 |

( 2 ) INFORMATION FOR SEQ ID NO:54:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:54:

```
Val Arg Glu Val Cys Ser Glu Gln Ala Glu Asp Gly His Cys Arg
 1               5                  10                  15

Ala Ala Ile Pro Arg Trp Tyr Phe Asp Val Thr Glu Gly Lys Cys
                20                  25                  30

Ala Pro Phe Phe Tyr Gly Gly Cys Gly Gly Asn Arg Asn Asn Phe
                35                  40                  45

Asp Thr Glu Glu Tyr Cys Ala Ala Val Cys Gly Ser Ala
                50                  55          58
```

( 2 ) INFORMATION FOR SEQ ID NO:55:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:55:

```
Val Arg Glu Val Cys Ser Glu Gln Ala Glu Asp Gly Pro Cys Arg
 1               5                  10                  15

Ala Ala Ile Pro Arg Trp Tyr Phe Asp Val Thr Glu Gly Lys Cys
                20                  25                  30

Ala Pro Phe Phe Tyr Gly Gly Cys Gly Gly Asn Arg Asn Asn Phe
                35                  40                  45

Asp Thr Glu Glu Tyr Cys Ala Ala Val Cys Gly Ser Ala
                50                  55          58
```

( 2 ) INFORMATION FOR SEQ ID NO:56:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:56:

```
Val Arg Glu Val Cys Ser Glu Gln Ala Glu Asp Gly Pro Cys Arg
 1               5                  10                  15

Ala Ala Ile Pro Arg Trp Tyr Phe Asp Val Thr Glu Gly Lys Cys
                20                  25                  30

Ala Pro Phe Ile Tyr Gly Gly Cys Gly Gly Asn Arg Asn Asn Phe
                35                  40                  45

Asp Thr Glu Glu Tyr Cys Ala Ala Val Cys Gly Ser Ala
                50                  55          58
```

( 2 ) INFORMATION FOR SEQ ID NO:57:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:57:

```
Val Arg Glu Val Cys Ser Glu Gln Ala Glu Asp Gly Arg Cys Arg
 1               5                  10                  15

Ala Ala Ile Pro Arg Trp Tyr Phe Asp Val Thr Glu Gly Lys Cys
```

```
                        20                         25                         30
Ala  Pro  Phe  Phe  Tyr  Gly  Gly  Cys  Gly  Gly  Asn  Arg  Asn  Asn  Phe
                         35                         40                         45

Asp  Thr  Glu  Glu  Tyr  Cys  Ala  Ala  Val  Cys  Gly  Ser  Ala
                         50                         55                   58
```

( 2 ) INFORMATION FOR SEQ ID NO:58:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:58:

```
Val  Arg  Glu  Val  Cys  Ser  Glu  Gln  Ala  Glu  Gly  Thr  Cys  Arg
  1                  5                        10                        15

Ala  Asn  Ile  Tyr  Arg  Trp  Tyr  Phe  Asp  Val  Thr  Glu  Gly  Lys  Cys
                         20                         25                         30

Ala  Pro  Phe  Phe  Tyr  Gly  Gly  Cys  Gly  Gly  Asn  Arg  Asn  Asn  Phe
                         35                         40                         45

Asp  Thr  Glu  Glu  Tyr  Cys  Ala  Ala  Val  Cys  Gly  Ser  Ala
                         50                         55                   58
```

( 2 ) INFORMATION FOR SEQ ID NO:59:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:59:

```
Val  Arg  Glu  Val  Cys  Ser  Glu  Gln  Ala  Glu  Leu  Gly  Gly  Cys  Arg
  1                  5                        10                        15

Ala  Trp  Ile  Leu  Arg  Trp  Tyr  Phe  Asp  Val  Thr  Glu  Gly  Lys  Cys
                         20                         25                         30

Ala  Pro  Phe  Phe  Tyr  Gly  Gly  Cys  Gly  Gly  Asn  Arg  Asn  Asn  Phe
                         35                         40                         45

Asp  Thr  Glu  Glu  Tyr  Cys  Ala  Ala  Val  Cys  Gly  Ser  Ala
                         50                         55                   58
```

( 2 ) INFORMATION FOR SEQ ID NO:60:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:60:

```
Val  Arg  Glu  Val  Cys  Ser  Glu  Gln  Ala  Glu  Pro  Gly  His  Cys  Arg
  1                  5                        10                        15

Ala  Ala  Ile  Pro  Arg  Trp  Tyr  Phe  Asp  Val  Thr  Glu  Gly  Lys  Cys
                         20                         25                         30

Ala  Pro  Phe  Phe  Tyr  Gly  Gly  Cys  Gly  Gly  Asn  Arg  Asn  Asn  Phe
                         35                         40                         45

Asp  Thr  Glu  Glu  Tyr  Cys  Ala  Ala  Val  Cys  Gly  Ser  Ala
                         50                         55                   58
```

( 2 ) INFORMATION FOR SEQ ID NO:61:

( i ) SEQUENCE CHARACTERISTICS:
        ( A ) LENGTH: 58 amino acids
        ( B ) TYPE: Amino Acid ( D ) TOPOLOGY: Linear ( x i ) SEQUENCE DESCRIPTION: SEQ ID NO:61:

```
Val  Arg  Glu  Val  Cys  Ser  Glu  Gln  Ala  Glu  Pro  Gly  Leu  Cys  Arg
 1              5                        10                        15

Ala  Ala  Phe  Pro  Arg  Trp  Tyr  Phe  Asp  Val  Thr  Glu  Gly  Lys  Cys
                    20                       25                        30

Ala  Pro  Phe  Phe  Tyr  Gly  Gly  Cys  Gly  Gly  Asn  Arg  Asn  Asn  Phe
                    35                       40                        45

Asp  Thr  Glu  Glu  Tyr  Cys  Ala  Ala  Val  Cys  Gly  Ser  Ala
                    50                       55        58
```

( 2 ) INFORMATION FOR SEQ ID NO:62:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:62:

```
Val  Arg  Glu  Val  Cys  Ser  Glu  Gln  Ala  Glu  Pro  Gly  Leu  Cys  Arg
 1              5                        10                        15

Ala  Ala  Ile  Tyr  Arg  Trp  Tyr  Phe  Asp  Val  Thr  Glu  Gly  Lys  Cys
                    20                       25                        30

Ala  Pro  Phe  Phe  Tyr  Gly  Gly  Cys  Gly  Gly  Asn  Arg  Asn  Asn  Phe
                    35                       40                        45

Asp  Thr  Glu  Glu  Tyr  Cys  Ala  Ala  Val  Cys  Gly  Ser  Ala
                    50                       55        58
```

( 2 ) INFORMATION FOR SEQ ID NO:63:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:63:

```
Val  Arg  Glu  Val  Cys  Ser  Glu  Gln  Ala  Glu  Pro  Gly  Leu  Cys  Arg
 1              5                        10                        15

Ala  Leu  Ile  Trp  Arg  Trp  Tyr  Phe  Asp  Val  Thr  Glu  Gly  Lys  Cys
                    20                       25                        30

Ala  Pro  Phe  Phe  Tyr  Gly  Gly  Cys  Gly  Gly  Asn  Arg  Asn  Asn  Phe
                    35                       40                        45

Asp  Thr  Glu  Glu  Tyr  Cys  Ala  Ala  Val  Cys  Gly  Ser  Ala
                    50                       55        58
```

( 2 ) INFORMATION FOR SEQ ID NO:64:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:64:

```
Val  Arg  Glu  Val  Cys  Ser  Glu  Gln  Ala  Glu  Pro  Gly  Arg  Cys  Arg
 1              5                        10                        15

Ala  Ala  Ile  Pro  Arg  Trp  Tyr  Phe  Asp  Val  Thr  Glu  Gly  Lys  Cys
                    20                       25                        30

Ala  Pro  Phe  Phe  Tyr  Gly  Gly  Cys  Gly  Gly  Asn  Arg  Asn  Asn  Phe
                    35                       40                        45

Asp  Thr  Glu  Glu  Tyr  Cys  Ala  Ala  Val  Cys  Gly  Ser  Ala
```

50           55          58

( 2 ) INFORMATION FOR SEQ ID NO:65:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:65:

```
Val Arg Glu Val Cys Ser Glu Gln Ala Glu Arg Gly His Cys Arg
 1               5                  10                  15

Ala Ala Ile Pro Arg Trp Tyr Phe Asp Val Thr Glu Gly Lys Cys
                20                  25                  30

Ala Pro Phe Phe Tyr Gly Gly Cys Gly Gly Asn Arg Asn Asn Phe
                35                  40                  45

Asp Thr Glu Glu Tyr Cys Ala Ala Val Cys Gly Ser Ala
                50                  55          58
```

( 2 ) INFORMATION FOR SEQ ID NO:66:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:66:

```
Val Arg Glu Val Cys Ser Glu Gln Ala Glu Thr Gly Pro Cys Arg
 1               5                  10                  15

Ala Ala His Ser Arg Trp Tyr Phe Asp Val Thr Glu Gly Lys Cys
                20                  25                  30

Ala Pro Phe Val Tyr Gly Gly Cys Gly Gly Asn Arg Asn Asn Phe
                35                  40                  45

Asp Thr Glu Glu Tyr Cys Ala Ala Val Cys Gly Ser Ala
                50                  55          58
```

( 2 ) INFORMATION FOR SEQ ID NO:67:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:67:

```
Val Arg Glu Val Cys Ser Glu Gln Ala Glu Thr Gly Pro Cys Arg
 1               5                  10                  15

Ala Ala His Ser Arg Trp Tyr Phe Asp Val Thr Glu Gly Lys Cys
                20                  25                  30

Ala Pro Phe Tyr Tyr Gly Gly Cys Gly Gly Asn Arg Asn Asn Phe
                35                  40                  45

Asp Thr Glu Glu Tyr Cys Ala Ala Val Cys Gly Ser Ala
                50                  55          58
```

( 2 ) INFORMATION FOR SEQ ID NO:68:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:68:

```
Val Arg Glu Val Cys Ser Glu Gln Ala Glu Thr Gly Pro Cys Arg
 1               5                  10                  15
```

Gly Ala His Ser Arg Trp Tyr Phe Asp Val Thr Glu Gly Lys Cys
            20                  25                  30

Ala Pro Phe Val Tyr Gly Gly Cys Gly Gly Asn Arg Asn Asn Phe
            35                  40                  45

Asp Thr Glu Glu Tyr Cys Ala Ala Val Cys Gly Ser Ala
            50                  55          58

( 2 ) INFORMATION FOR SEQ ID NO:69:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:69:

Val Arg Glu Val Cys Ser Glu Gln Ala Glu Thr Gly Pro Cys Arg
1               5                   10                  15

Gly Ala His Ser Arg Trp Tyr Phe Asp Val Thr Glu Gly Lys Cys
            20                  25                  30

Ala Pro Phe Trp Tyr Gly Gly Cys Gly Gly Asn Arg Asn Asn Phe
            35                  40                  45

Asp Thr Glu Glu Tyr Cys Ala Ala Val Cys Gly Ser Ala
            50                  55          58

( 2 ) INFORMATION FOR SEQ ID NO:70:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:70:

Val Arg Glu Val Cys Ser Glu Gln Ala Glu Thr Gly Pro Cys Arg
1               5                   10                  15

Ala Leu His Ser Arg Trp Tyr Phe Asp Val Thr Glu Gly Lys Cys
            20                  25                  30

Ala Pro Phe Tyr Tyr Gly Gly Cys Gly Gly Asn Arg Asn Asn Phe
            35                  40                  45

Asp Thr Glu Glu Tyr Cys Ala Ala Val Cys Gly Ser Ala
            50                  55          58

( 2 ) INFORMATION FOR SEQ ID NO:71:

( i ) SEQUENCE CHARACTERISTICS:
        ( A ) LENGTH: 58 amino acids
        ( B ) TYPE: Amino Acid
        ( D ) TOPOLOGY: Linear ( x i ) SEQUENCE DESCRIPTION: SEQ ID NO:71:

Val Arg Glu Val Cys Ser Glu Gln Ala Glu Thr Gly Pro Cys Arg
1               5                   10                  15

Ala Asn His Ser Arg Trp Tyr Phe Asp Val Thr Glu Gly Lys Cys
            20                  25                  30

Ala Pro Phe Ser Tyr Gly Gly Cys Gly Gly Asn Arg Asn Asn Phe
            35                  40                  45

Asp Thr Glu Glu Tyr Cys Ala Ala Val Cys Gly Ser Ala
            50                  55          58

( 2 ) INFORMATION FOR SEQ ID NO:72:

( i ) SEQUENCE CHARACTERISTICS:

( A ) LENGTH: 9 amino acids
( B ) TYPE: Amino Acid
( D ) TOPOLOGY: Linear ( x i ) SEQUENCE DESCRIPTION: SEQ ID NO:72:

| Asp | Gly | His | Cys | Arg | Ala | Ala | His | Pro |
|-----|-----|-----|-----|-----|-----|-----|-----|-----|
| 1   |     |     |     | 5   |     |     |     | 9   |

USE OF KUNITZ TYPE PLASMA KALLIKREIN INHIBITORS

FIELD OF THE INVENTION

This invention relates to novel polypeptides which comprise at least one Kunitz-type domain having plasma kallikrein inhibitory activity. The invention further relates to the DNA encoding these novel polypeptides, and the recombinant materials and methods for producing these plasma kallikrein inhibitors. The invention also relates to pharmaceutical compositions containing the novel plasma kallikrein inhibitors for the treatment of diseases and disorders where the inhibition of plasma kallikrein is indicated.

DESCRIPTION OF RELATED ART

Kallikrein

Kallikrein is a serine protease of the multicomponent coagulation cascade that participates in the contact system of the intrinsic pathway of blood coagulation. Kallikrein also cleaves high molecular weight kininogen (HMWK) to form bradykinin (a potent vasodilator and endothelial cell activator), can activate prourokinase and plasminogen (fibrinolytic), and feeds back for reciprocal activation of surface bound Factor XII to Factor XIIa. In addition, it can also stimulate neutrophils causing the release of elastase. Both Factor XIIa and kallikrein can lead to plasmin generation causing fibrinolysis. Thus, although it plays a central role in the contact activation pathway, plasma kallikrein is involved in both fibrin deposition and lysis, modulation of blood pressure, complement activation and support of the inflammatory system. For a review of the contact activation pathway and kallikrein-kinin system see Bhoola, K. D., et al., (1992), Pharmacological Rev., 44(1):1–80; and Wachtfogel, Y. T., (1993), Thromb. Res., 72:1–21.

Prekallikrein, the precursor of kallikrein, is a glycoprotein comprised of a single polypeptide chain with a molecular weight of 80,000 Da and is present in normal plasma at a concentration of ca. 50 μ/ml (600 nM). In blood, 75% of prekallikrein circulates bound to high molecular weight kininogen (HMWK). Kallikrein consists of 2 disulfide bonded chains of 43,000 and 33,000–36,000 Da. The light chain of kallikrein contains the enzymatic domain while the heavy chain appears to be required for surface dependent activation of coagulation.

Because of its role in a diverse array of biological functions, regulation of plasma kallikrien as a form of therapeutic intervention has been extensively studied.

Contact Activation Pathways in Disease

Contact activation is a surface mediated pathway responsible in part for the regulation of inflammation and coagulation. The proteins involved in this pathway include Factor XII (Hageman Factor), prekallikrein (Fletcher Factor), high molecular weight kininogen (HMWK), and C1 inhibitor (Schmaier, A. H. et al., in *Hemostasis and Thrombosis: Basic Principles and Clinical Practice* (Colman, R. W., Hirsh, J., Marder, V., & Salzman, E. W., Eds.) 1987, pp 18–38, J. B. Lippincott Co., Philadelphia). The zymogens Factor FXII and prekallikrein are converted into active serine proteases as initial events in this pathway. The involvement of this plasma protease system has been suggested to play a significant role in a variety of clinical manifestations including septic shock, adult respiratory distress syndrome (ARDS), disseminated intravascular coagulation (DIC) and various other disease states (Coleman R. W. (1989) N. Engl. J. Med 320:1207–1209; Bone, R. C. (1992) Arch. Intern. Med. 152:1381–1389).

The contact system of intrinsic coagulation and the complement system are excessively activated in sepsis and septic shock, especially in cases of fatal septic shock. The contact system can participate in the generation of many vasoactive mediators such as bradykinin, FXIIa, FXIIf and C5a, which are thought to play a role in the pathogenesis of fatal shock. Bradykinin, FXIIa, and XIIf are potent inducers of hypotension while C5a is an inducer of vasodilation and vasopermeability. The levels of FXII, prekallikrein, and high molecular weight kininogen are decreased significantly during non-fatal shock, but are most severely depressed during fatal septic shock to approximately 30%, 57% and 27% of normal values respectively. These changes are noted regardless of whether the septic state is caused by gram positive or gram negative bacteria.

The contact activation pathway is also involved in both fibrin deposition and lysis, as well as triggering neutrophil activation, activation of complement and modulation of blood pressure.

Septic shock

Septic shock is the most common cause of death of humans in intensive care units in the United States (Parillo, J. E. et al., (1990), Ann. Int. Med. 113:227–242; Schmeichel C. J. & McCormick D., (1992) BioTechnol. 10:264–267). It is usually initiated by a local nidus of infection that invades the blood stream. Incidences of sepsis and shock can arise from infections with either gram negative, gram positive bacterial or fungal microorganisms. All these organisms seem to induce a common pattern of cardiovascular dysfunction. In recent years aggressive fluid infusion therapy has been accepted as a primary means of treatment for septic shock. Adequate repletion of fluid is associated with an elevated cardiac output and low vascular resistance. Despite treatment, septic shock results in a severe decrease in systemic vascular resistance and generalized blood flow maldistribution. Aggressive therapy reverses shock and death in about 50% of the cases. Unresponsive hypotension resulting from a very low vascular resistance cannot be corrected by fluid infusion. Among those subjects that die from septic shock, approximately 75% die from persistent hypotension and the remainder due to multiple organ system failure.

The increase in cardiac output and vasodilation in septic shock is attributed to the action of inflammatory mediators. In septic shock, components of the kallikrein-kinin system are depleted suggesting activation of this system. This is not the case in cardiogenic shock suggesting that the kallikrein-kinin system is a key player in septic shock (Martinez-Brotons F. et al., (1987) Thromb. Haemostas. 58:709–713). While the actual events leading to septic shock, DIC and hypotension have not been established, the known interactions among various components of the many physiological systems suggest that activation of the contact pathway may lead to a state of septic shock, multiorgan failure, and death (Bone, R. C., supra) as illustrated in FIG. 1.

ARDS

ARDS is a complex pulmonary disorder affecting 150,000 people in the U.S. yearly with a 50 % mortality rate. Leukocytes, platelets and the proteolytic pathways of coagulation and complement mediate ARDS. ARDS involves activation of the contact activation pathway and depletion of C1 inhibitor. Sepsis induced ARDS results in more severe DIC and fibrinolysis, more fibrin degradation products and reduced ATIII levels compared to trauma induced ARDS (Carvalho, A. C. et al., (1988) J. Lab. Clin. Med. 112:270–277).

Disseminated Intravascular Coagulation

Disseminated intravascular coagulation (DIC) is a disorder that occurs in response to tissue injury and invading microorganisms characterized by widespread deposition of fibrin and depleted levels of fibrinogen (Muller-Berghaus, G. (1989) Semin. Thromb. Hemostasis, 15:58–87). There are prolonged prothrombin and activated partial thromboplastin times. DIC has been observed in the clinical settings of a wide variety of diseases (Fruchtman, S. M. & Rand, J. H. in *Thrombosis in Cardiovascular Disorders*, Fuster, V. & Verstraete M. eds., (1992) pp 501–513 W. B. Saunders, Philadelphia).

Hypotension, DIC, and neutrophil activation are all triggered by the interaction of Factor XIIa, plasma kininogens and kallikrein. Deficiency of any of these 3 proteins does not give rise to hemostatic disorders due to redundancy in the system due to platelets, other coagulation factors, and endothelial cells.

Plasma Kallikrein Inhibitors

A large number of therapeutic approaches to septic shock and related disorders have been identified including various cytokine antagonists, Mabs (to endotoxin, tissue factor, tumor necrosis factor (TNF), neutrophils, etc.), kinin antagonists, bacteriocidal permeability increasing protein, PAF antagonists, C1 inhibitor, DEGR-FXa, and activated protein C, among others. It is possible, due to the complicated nature of the disease, that an approach that involves multiple agents or agents that affect multiple pathways may be successful in the treatment of septic shock (Schmeichel C. J. & McCormick D., supra). Potent serine protease inhibitors that reversibly inhibit proteases of the coagulation, contact activation, fibrinolysis, inflammation, complement activation, and hypotensive pathways are one approach to the treatment of diseases that are affected by these pathways.

Protein inhibitors play critical roles in the regulation of proteases in a wide variety of physiological processes. The major physiological inhibitor of plasma kallikrein is C1 inhibitor, a serpin which results in irreversible inhibition. C1 inhibitor is also the major physiological inhibitor of FXIIa, and the complement pathway proteases C1r and C1 s. α2-macroglobulin, another major inhibitor of kallikrein, inhibits the kinin-forming function while only partially inhibiting esterolytic activity. Antithrombin-III can also inhibit kallikrein, but slowly even in the presence of heparin. α2-antiplasmin and α1-antitrypsin are poor inhibitors of kallikrein. A mutant form of $\alpha_1$-proteinase inhibitor ($\alpha_1$-proteinase inhibitor-Pittsburgh) that contains an Arg in the $P_1$ position and an Ala in the $P_2$ position has been shown to be a more potent inhibitor of Factor XIIf (FXIIf) and kallikrein compared to C1 inhibitor, the most potent known natural inhibitor of these proteases (Schapira, M. et al., (1987) J. Clin. Invest 80:582–585; Patston, P. A. et al., (1990) J. Biol. Chem. 265:10786–10791). Rats treated with this mutant were partially protected from the hypotension resulting from injection of FXIIf.

Recently, ecotin, a 142 residue protein from *E. coli*, has been shown to potently inhibit plasma kallikrein with a $K_i$ of ca. 160 pM; however ecotin is not totally selective and also potently inhibits Factor XIIa, Factor Xa and human leukocyte elastase (Seymour, J. L., et al., (1994) Biochemistry 33:3949–3958).

Bovine pancreatic trypsin inhibitor (BPTI, aprotinin) is a well-studied member of the Kunitz domain family of serine protease inhibitors that moderately inhibits plasma kallikrein with $K_i$ of ca. 30 nM (Fritz, H., and Wunderer, G., (1983) Arzeim.-Forsch. Drug Res. 33:479–494; Creighton, T. E., and Charles, I. G. (1987) Cold Spring Harbor Symp. Quant. Biol. 52:511–519). However, BPTI is a more potent inhibitor of plasmin.

Aprotinin has been used in a wide variety of clinical states including acute pancreatitis, septic and hemorrhagic shock, adult respiratory distress syndrome and multiple trauma; recently it has shown promise both clinically and in models of cardiopulmonary bypass (Westaby, S., (1993) Ann. Thorac. Surg. 55:1033–1041; Watchfogel, T., et al., (1993) J. Thorac. Cardiovasc. Surg. 106:1–10).

As a broad spectrum Kunitz type serine protease inhibitor, aprotinin can prevent activation of the clotting cascade initiated by the contact activation pathway. It can also prevent activation of neutrophils and other inflammatory responses resulting from tissue damage caused by ischemia and hypoxia. These benefits are believed to be derived from its kallikrein or plasmin inhibitory activity; however, the fact that aprotinin is neither very potent nor selective make it difficult to interpret these effects.

Aprotinin inhibits the contact, neutrophil, and platelet activation systems during simulated extracorporeal perfusion as evidenced by a reduction in blood loss, prevention of neutrophil degranulation, platelet activation and aggregation, and formation of kallikrein-Cq-inhibitor and C1—C1 inhibitor complexes (Watchfogel, et al., (1993) J. Thorac. Cardiovasc. Surg. 106:1–10). It has been used to inhibit plasma kallikrein during LPS induced endotoxic shock in pigs with the result of preventing arterial hypotension (Seibeck, M. et al., (1993) J. Trauma 34:193–198). Aprotinin has also been used to investigate the involvement of the plasma kallikrein-kinin system in the haemodynamic and renal function in patients with hepatic cirrhosis (MacGilchrist, A., (1994) Clin. Sci. 87:329–335). Aprotinin has been shown to be beneficial to renal hydrodynamics resulting in improved renal flow and filtration.

Trasylol® (aprotinin, Bayer AG, Leverkusen, Germany) is currently indicated to inhibit the contact system of plasma which is massively activated on the first passage of blood through the cardiopulmonary bypass circuit during bypass procedures (Westaby, S. (1993) Ann. Thorac. Surg. 55:1033–41). Aprotinin blocks contact activation of the kallikrein system during cardiopulmonary bypass and acts in synergy with heparin in preventing thrombus formation through inhibition of the intrinsic clotting cascade (Westaby, supra). Trasylol® has also been used prophylactically in septic shock, haemorrhagic shock, post operative necrotic pancreatitis, and post operative pulmonary embolism.

Kunitz Domains

Kunitz-type serine protease inhibitors (BPTI, Aprotinin, for example) are a well characterized family of proteins that exhibit extensive structural homology including a characteristic tertiary fold containing an extended binding loop that fits into the active site of the cognate serine protease (Bode, W., and Huber, R., (1992) Eur. J. Biochem. 204:433–451). Kunitz type serine protease inhibitors are known to be slow, tight-binding, reversible inhibitors of serine proteases that bind to the active site and inhibit according to the standard mechanism (Laskowski, Jr., M. and Kato, I., (1980) Ann. Rev. Biochem. 49:593–626). Cleavage between the $P_1$ and $P_1'$ residues occurs very slowly if at all (Bode, W. and Huber, R., (1992) Eur. J. Biochem. 204:433–451; Laskowski, M., Jr. and Kato, I., (1980) Annu. Rev. Biochem. 49:593–626; The $P_1$ residue refers to the position preceding the scissile peptide bond of the substrate or inhibitor and fits into the $S_1$ binding site as defined by Schecter and Berger (1967) Biochem. Biophys. Res. Commun., 27:157–162. The residue numbering corresponds to that of BPTI such that residue 15 is at the $P_1$ position).

Some of the contact residues in the binding loop (positions 11, 15, 17, and 19) are relatively variable among Kunitz domains (Creighton, T. E. and I. G. Charles, (1987) Cold Spring Harbor Symp. Quant. Biol. 52:511–519). Position 13 is normally a Pro. Position 12 is almost always a Gly. The cysteine residues at positions 14 and 38 that form a disulfide bond are always found in Kunitz domains; however other residues such as Ala, Gly, Ser, or Thr may substitute for the cysteines (Marks, C. B. et al., (1987) Science, 235: 1370–1373).

In the 58 residue Kunitz protease inhibitor domain of the Alzheimer's amyloid β-protein precursor (APPI) and other Kunitz domains, residues 13 and 39 as well as residues 17 and 34 are in close proximity (FIG. 3) (Hynes, T. R. et al., (1990)Biochemistry 29: 10018–10022). Residues at positions 16 and 18 are generally more invariant among Kunitz domains (Creighton, T. E. and I. G. Charles, (1987) Cold Spring Harbor Symp. Quant. Biol. 52:511–519); however, different residues at these positions may also alter binding. Therefore, residues at positions 11 through 19, 34, 38, and 39 may all affect the binding affinity and specificity towards serine proteases (FIG. 3).

Other residues are important as well. For instance, APPI and BPTI have a methionine at position 52, although other Kunitz domains have a variety of residues at this position (FIG. 2). Methionine at this position can be replaced by different residues which may be beneficial with respect to producing the protein. For example, methionine is susceptible to oxidation to form methionine sulfoxide, which can complicate purification. Also protein can be made recombinantly as a fusion protein, followed by cleavage with CNBr, which cleaves at methionine residues (Auerswald, E. A. et al., (1988) Biol. Chem. Hoppe-Seyler 369: 27–35). Therefore, it is necessary to remove other methionine residues in the protein of interest to produce intact product. Substitutions at position 52 are not expected to have major effects on inhibitory activity since it is so far away from the primary binding loop of the Kunitz domain (FIG. 3).

Substrates and inhibitors of trypsin-like proteases such as kallikrein and FXIa have either Arg or Lys at the $P_1$ residue (EP O 339 942 A2). However methionine is sometimes found at the $P_1$ position and may also be preferable for good inhibition of serine proteases (McGrath, M. E. et al., (1991) J. Biol. Chem. 266:6620–6625). The introduction of residues such as Val, Leu, or Ile at the $P_1$ position of Kunitz domains leads to potent inhibitors of human leukocyte elastase (HLE) and concomitant loss of the wild type inhibitory activity (Beckmann, J. et al., (1991) Eur. J. Biochem. 176:675–682; Sinha, S. et al., (1991) J. Biol. Chem. 266:21011–21013).

Recently, APPI, which is structurally similar to BPTI (Hynes, T., et al., (1990) Biochemistry 29:10018–10022), was used as a scaffold for phage display of a large library of variants to select potent and specific active site inhibitors of tissue factor-Factor VIIa (TF-FVIIa) (Dennis, M.S., and Lazarus, R. A., (1994) J. Biol. Chem. 269:22129–22136; Dennis, M. S., and Lazarus, R. A., (1994) J. Biol. Chem. 269:22137–22144). A direct comparison of variants produced in that study against tissue factor-Factor VIIa showed a 95-fold increase in binding affinity for plasma kallikrein by changing the $P_1$ residue from Lys to Arg. The data were not inconsistent with those presented earlier for BPTI where Arg and Lys were studied at position $P_1$ (Scott, C. F., et al., Blood 69:1431–1436). In this study, a change of Lys to Arg at position $P_1$ resulted in a 20 fold more potent inhibitor of plasma kallikrein. Neither of these studies suggested a specific inhibitor of plasma kallikrein since the proteases demonstrated inhibition of other serine proteases such as tissue factor-Factor VIIa, Factor XIa or plasmin.

APPI has been readily expressed in bacteria such as *E. coli* (Castro, M. et al., (1990) FEBS Lett. 267:207–212) and yeast such as P. pastoris. The x-ray crystal structure of the protein is known (Hynes, T. R. et al., (1990) Biochemistry 29:10018–10022). Additionally, it is derived from a human sequence, which would minimize the immunogenicity for any therapeutically useful variants.

Despite recent advances, there remains a need for potent specific inhibitors of plasma kallikrein for the development of targeted therapeutic tools.

summary of the Invention

The present invention provides for compositions capable of potent reversible inhibition of proteases of the coagulation, contact activation, fibrinolysis, inflammation, complement activation, and hypotensive pathways. In particular the invention provides for the potent inhibition of plasma kallikrein. The compositions of the present invention comprise a serine protease inhibitor polypeptide. The polypeptide inhibitor of the present invention comprises at least one non-native Kunitz-type serine protease inhibitor domain capable of the potent inhibition of plasma kallikrein.

In a preferred embodiment the invention provides for a polypeptide comprising at least one non-native Kunitz-type is serine protease inhibitor domain said Kunitz-type serine protease inhibitor domain having a primary binding loop:

$Xaa_5\text{-}Xaa_4\text{-}Xaa_3\text{-}Xaa_2Xaa_1\text{-}Xaa_1'\text{-}Xaa_2'\text{-}Xaa_3'\text{-}Xaa_4'$ and a secondary binding loop comprising:

$Xaa_{19}'$ wherein $Xaa_5$ is an amino acid selected from the group consisting of Pro, Asp, Glu, Ser, Thr, Arg, and Leu; $Xaa_4$ is the amino acid Gly; $Xaa_3$ is an amino acid selected from the group consisting of His, Pro, Arg, Leu, Gly, and Thr; $Xaa_2$ is Cys; $Xaa_1$ is Arg; $Xaa_1'$ is an amino acid selected from the group consisting of Ala and Gly; $Xaa_2'$ is an amino acid selected from the group consisting of Arg, Leu, Asn, Trp and Ser; $Xaa_3'$ is an amino acid selected from the group consisting of His and Ile; $Xaa_4'$ is selected from the group consisting of Pro, Tyr, Leu, and Trp; and $Xaa_{19}'$ is an amino acid selected from the group consisting of Val, Tyr, Trp, Ser, and Phe.

In a further preferred aspect of the present invention the polypeptide comprises a Kunitz-type serine protease inhibitor domain having the sequence:

$R_1\text{-}Xaa_5\text{-}Xaa_4\text{-}Xaa_3\text{-}Xaa_2\text{-}Xaa_1\text{-}Xaa_1'\text{-}Xaa_2'\text{-}Xaa_3'\text{-}Xaa_4'\text{-}R_2\text{-}Xaa_{19}'\text{-}R_3$ where $R_1$ is a 10 amino acid peptide and the amino acid corresponding to amino acid position $Xaa_{11}$ is Cys; $R_2$ is a 14 amino acid peptide wherein the amino acid corresponding to amino acid position $Xaa_{15}'$ is Cys; and $R_3$ is a 24 amino acid peptide wherein the amino acids corresponding to amino acid positions $Xaa_{23}'$, $Xaa_{36}'$ and $Xaa_{40}'$ are Cys. According to this aspect of the present invention the polypeptide of the present invention comprises a Kunitz-type domain of approximately 58 amino acids having a primary binding loop comprising amino acids $Xaa_5\text{-}Xaa_4\text{-}Xaa_3\text{-}Xaa_2\text{-}Xaa_1\text{-}Xaa_1'\text{-}Xaa_2'\text{-}Xaa_3'\text{-}Xaa_4'$, and a secondary binding loop comprising amino acid $Xaa_{19}'$ as defined above for the invention.

Exemplary Kunitz type domains have an $R_1$ selected from the group consisting of
VREVCSEQAE (SEQ ID NO: 6),
MHSFCAFKAD (SEQ ID NO: 7),
KPDFCFLEED (SEQ ID NO: 8),
GPSWCLTPAD (SEQ ID NO: 9), KEDSCQLGYS (SEQ ID NO: 10),
TVAACNLPIV (SEQ ID NO: 11),
LPNVCAFPME (SEQ ID NO: 12), and
RPDFCLEPPY (SEQ ID NO: 13);

$R_2$ is selected from the group consisting of
RWYFDVTEGKCAPF (SEQ ID NO: 14),
RFFFNIFTRQCEEF (SEQ ID NO: 15),
RYFYNNQTKQCERF (SEQ ID NO: 16),
RFYYNSVIGKCRPF (SEQ ID NO: 17),
RYFYNGTSMACETF (SEQ ID NO: 18),
LWAFDAVKGKCVLF (SEQ ID NO: 19),
KWYYDPNTKSCARF (SEQ ID NO: 20),
RWFFNFETGECELF (SEQ ID NO: 21), and
RYFYNAKAGLCQTF (SEQ ID NO: 22); and $R_3$ is selected from the group consisting of
YGGCGGNRNNFDTEEYCAAVCGSA (SEQ ID NO: 23),
YGGCGGNRNNFDTEEYCMAVCGSA (SEQ ID NO: 24),
YGGCEGNQNRFESLEECKKMCTRD (SEQ ID NO: 25),
YGGCLGNMNNFETLEECKNICEDG (SEQ ID NO: 26),
YSGCGGNENNFTSKQECLRACKKG (SEQ ID NO: 27),
YGGCMGNGNNFVTEKECLQTCRTV (SEQ ID NO: 28),
YGGCQGNGNKFYSEKECREYCGVP (SEQ ID NO: 29),
YGGCGGNENKFGSQKECEKVCAPV (SEQ ID NO: 30),
YGGCGGNSNNFLRKEKCEKFCKFT (SEQ ID NO: 31), and
YGGCRAKRNNFKSAEDCMRTCGGA (SEQ ID NO: 32).

Preferred polypeptides also include polypeptides that inhibit plasma kallikrein and comprise a Kunitz type serine protease inhibitor domain having a primary and secondary binding loop as described above and wherein RI represents amino acid residues 1–10 of APPI (SEQ ID NO: 6) or conservative amino acid substitutions thereof; $R_2$ represents amino acid residues 20–33 of APPI (SEQ ID NO: 14) or conservative amino acid substitutions thereof; and $R_3$ represents amino acid residues 35 through 58 of APPI (SEQ ID NO: 24) or conservative amino acid substitutions thereof.

In a preferred aspect the polypeptide comprises a Kunitz-type serine protease inhibitor domain having a primary binding loop $Xaa_5$-$Xaa_4$-$Xaa_3$-$Xaa_2$-$Xaa_1$-$Xaa_1'$-$Xaa_2'$-$Xaa_3'$-$Xaa_4'$ wherein $Xaa_5$ is an amino acid selected from the group Glu, Asp, and Pro; $Xaa_4$ is Gly; $Xaa_3$ is His; $Xaa_2$ is Cys; $Xaa_1$ is Arg; $Xaa_1'$ is Ala; $Xaa_2'$ is Ala; $Xaa_3'$ is His; and $Xaa_4'$ is Pro; and a secondary binding loop comprising $Xaa_{19}'$ where $Xaa_{19}'$ is selected from Val, Trp and Tyr.

According to the present invention, the serine protease inhibitors are capable of the potent inhibition of plasma kallikrein. Therefore, a preferred polypeptide within the context of the present invention has an apparent dissociation constant ($K_i^*$) for plasma kallikrein of less than about 500 picomolar (pM). More preferably, the polypeptides of the present invention have a Ki for plasma kallikrein of less than about 300 pM and most preferably less than about 100 pM. In a preferred aspect of the present invention the serine protease inhibitors are capable of the potent and specific inhibition of plasma kallikrein. According to this aspect of the present invention the serine protease inhibitors inhibit plasma kallikrein and are not capable of appreciable inhibition of other serine proteases of the coagulation cascade such as Factor Xa, tissue factor-Factor VIIa, thrombin, Factor XIIa, or activated protein C.

In a further embodiment, the present invention encompasses a composition of matter comprising isolated nucleic acid, preferably DNA, encoding the polypeptide of the invention. The invention further comprises an expression control sequence operably linked to the DNA molecule, an expression vector, preferably a plasmid, comprising the DNA molecule, where the control sequence is recognized by a host is cell transformed with the vector, and a host cell transformed with the vector.

Preferred expression vectors of the present invention may be selected from, for example; pBR322, phGH1, pBO475, pRIT5, pRIT2T, pKK233-2, pDR540, and pPL-lambda, with the most preferred vector being pSAlz1.

Preferred host cells containing the expression vector of the present invention may be selected from, for example, E. coli K12 strain 294 (ATCC No. 31446), E. coli strain JM101, E. coli B, E. coli X1776 (ATCC No. 31537), E. coli c600, E. coli W3110 (F-, gamma-, prototrophic, ATCC No. 27325), Bacillus subtilis, Salmonella typhimurium, Serratia marcesans, and Pseudomonas species, with the most preferred host cell being E. coli W3110 (ATCC No. 27325), or a derivative thereof such as the protease deficient strain 27C7 (ATCC No. 55244).

The composition of the present invention may be made by a process which includes the steps of isolating or synthesizing nucleic acid sequences encoding any of the amino acid sequences described above, ligating the nucleic acid sequence into a suitable expression vector capable of expressing the nucleic acid sequence in a suitable host, transforming the host with the expression vector into which the nucleic acid sequence has been ligated, and culturing the host under conditions suitable for expression of the nucleic acid sequence, whereby the protein encoded by the selected nucleic acid sequence is expressed by the host. Preferably, the polypeptide is then recovered from the host cell culture. In this process, the ligating step may further contemplate ligating the nucleic acid into a suitable expression vector such that the nucleic acid is operably linked to a suitable secretory signal, whereby the amino acid sequence is secreted by the host. The secretory signal may be selected from the group consisting of the leader sequence, for example, of stII, lamB, herpes gD, lpp, alkaline phosphatase, invertase, and alpha factor and is preferably stII.

The present invention further extends to therapeutic applications for the compositions described herein. Thus the invention includes a pharmaceutical composition comprising a pharmaceutically acceptable excipient and the purified polypeptide of the invention.

Those applications include, for example, a method of treating a mammal for which inhibiting plasma kallikrein is indicated comprising administering a pharmaceutically effective amount of the pharmaceutical composition to the mammal. Such indications include; inflammation, septic shock, hypotension, ARDS, DIC, cardiopulmonary bypass surgery, and bleeding from postoperative surgery.

DESCRIPTION OF THE DRAWINGS

FIG. 2. Sequence alignment of Kunitz domains from mammalian sources. Aligned are. APPI (residues 1–58) (SEQ ID NO: 34) from human Alzheimer's disease amyloid β-protein precursor, residues 287–344 (Castro, M. et al. (1990) FEBS Lett. 267:207–212); TFPI-KD1 (Kunitz domain 1)(residues 22–79) (SEQ ID NO: 35), TFPI-KD2 (residues 93–150) (SEQ ID NO: 36), and TFPI-KD3 (residues 185–242) (SEQ ID NO: 37) of human TFPI (tissue factor protein inhibitor or LACI, Broze Jr., G. J. et al., (1990) Biochemistry 29:7539–7546); ITI-KD1 and ITI-KD2, (residues 22–79 and 78–135) (SEQ ID NO: 38 and 39) of human inter-α-trypsin inhibitor, respectively (Vetr, H. et al., (1989) FEBS Lett. 245:137–140); Collagen α 3 (VI) (residues 2899–2956) (SEQ ID NO: 40) of Collagen α 3 (VI) chain precursor (Chu, M. L. (1990) et al. EMBO J. 9:385–393); HKIB9 (7–60) (SEQ ID NO: 41) Human Kunitz-type protease inhibitor, HKIB9 (Norris, K., in Genbank Database (Dec. 31, 1993, Release 39.0), submitted Jan. 19,1994); BPTI (1–58) (SEQ ID NO: 42), Aprotinin or bovine basic pancreatic trypsin inhibitor (Creighton T. E. and Charles, I. G., (1987) Cold Spring Harbor Symp. Quant. Biol. 52:511–519). A motif alignment of invariant residues is also listed.

DETAILED DESCRIPTION OF THE INVENTION

I. Definitions

Abbreviations used throughout the description include: FXIIa for Factor XIIa; HMWK for high molecular weight kininogen; FXIa for Factor XIa; FXa for Factor Xa; TF for tissue factor; FVIIa for Factor VIIa; BPTI for basic pancreatic trypsin inhibitor; APPI for Alzheimer's amyloid β-protein precursor inhibitor; $K_i^*$ for apparent equilibrium dissociation constant; BSA for bovine serum albumin; HPLC for high performance liquid chromatography; PT for prothrombin time; APTT for activated partial thromboplastin time.

Figure 3:
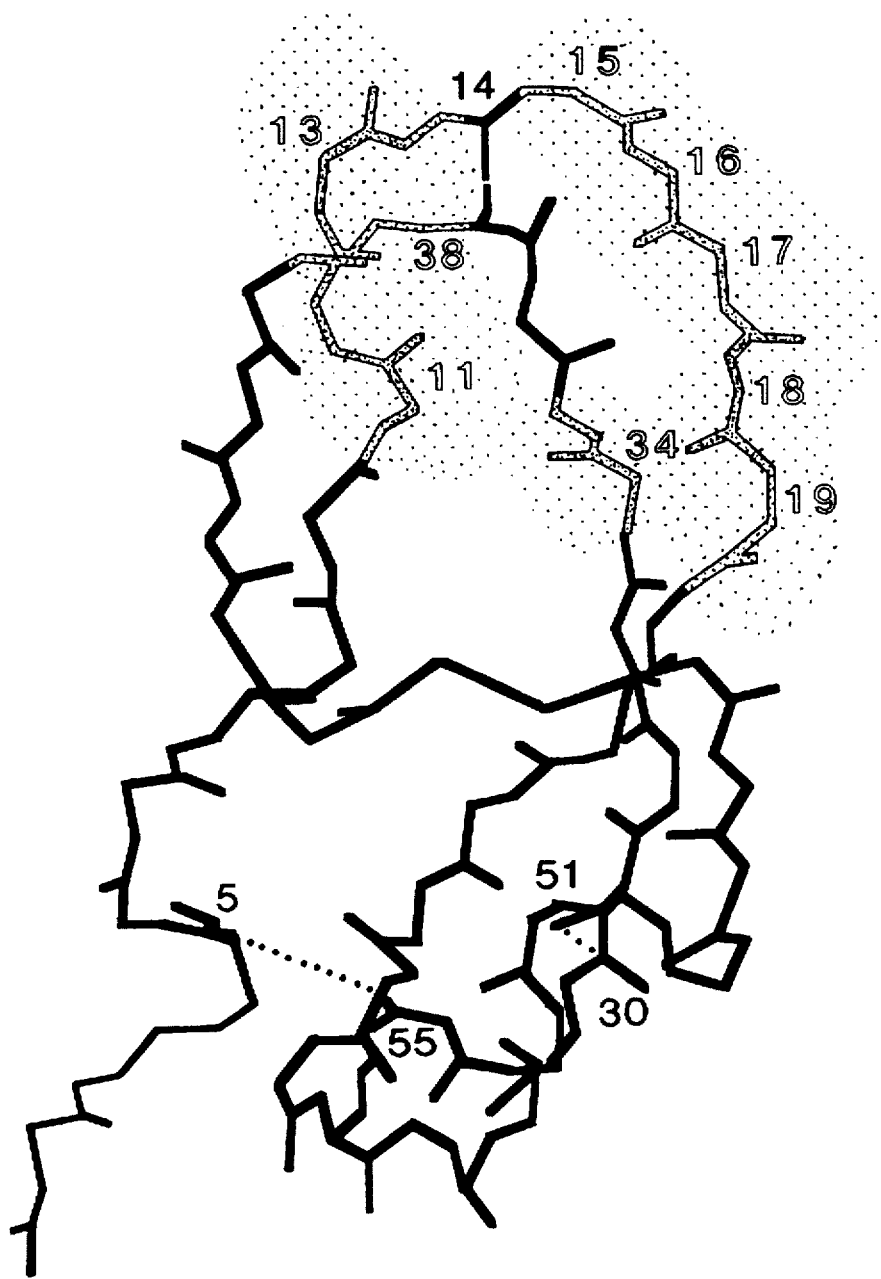
FIG. 3. Model of APPI and other Kunitz domains. The numbers refer to the residues found in APPI and other Kunitz domains; residue 15 corresponds to the $P_1$ residue. The shaded area refers to the primary (residues 11–19) and secondary (comprising residue 34) binding loops of APPI and other Kunitz domains. Disulfide bonds between cysteine residues at positions 14 and 38, 5 and 55, and 30 and 51, are indicated as dashed lines.

The terms "Kunitz-type serine protease inhibitor domain," "Kunitz-type domain," "Kunitz domain," and the like are used interchangeably herein to refer to an approximately 58 amino acid residue protein domain characterized by a conservation of cysteine residues with the serine protease inhibitor BPTI (bovine pancreatic trypsin inhibitor; Creighton and Charles, (1987) Cold Spring Harbor Symp. Quant. Biol. 52:511–519) first isolated in crystalline form in 1936 (Kunitz, M., and Northop, J. H., (1936) J. Gen. Physiol. 19:991–1007). Kunitz domains share cysteine residue placement, tertiary folding, and structural characteristics. FIG. 3 is a model of the tertiary structure of the Kunitz domain of Alzeheimer's amyloid β-protein precursor showing cysteine residue placement.

Figure 2:
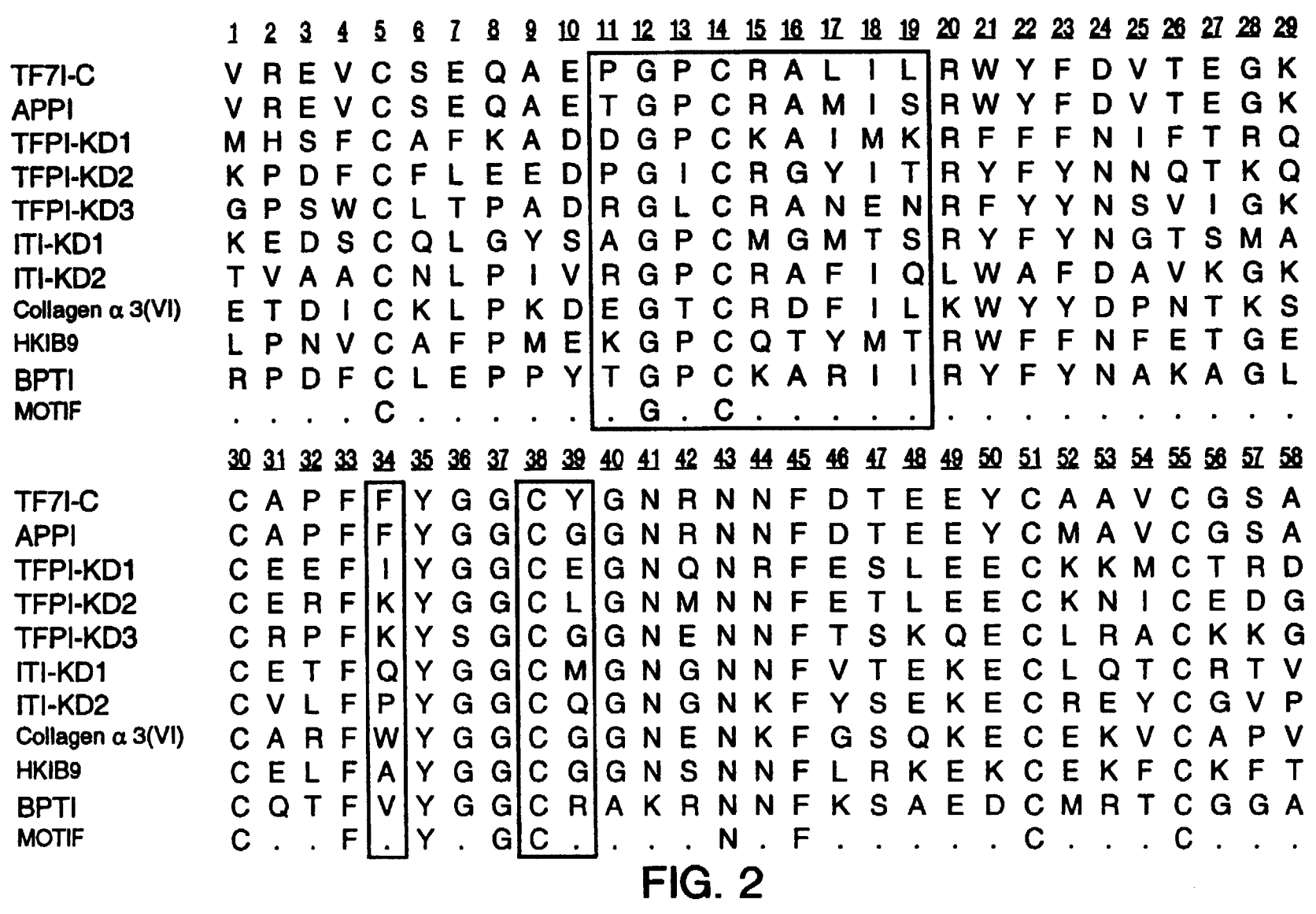

A family of proteins has been identified containing one, two or three Kunitz domains. The family includes; LACI (lipoprotein-associated coagulation inhibitor, also TFPI or tissue factor protein inhibitor; Broze, Jr. G. J., et al., (1990) Biochemistry 29:7539–7546); APPI (Alzheimer's amyloid β-protein precursor; Hynes, T. R., (1990) Biochemistry 29:10018–10022); the α-3 chain of human type VI collagen (see WO 93/14119) and inter-α-trypsin inhibitor (Hochstrasser, K., E., (1985) Biol. Chem. Hoppe-Seyler 366:473). FIG. 2 presents the sequence alignment of Kunitz domains from mammalian sources. Kunitz-type domains have also been identified in red sea turtle egg white, chelonianin (Kato, I., and Tominaga, N., (1979) Fed. Proc. 38:3342–3357), and B-chain of $β_1$ bungarotoxin (Kondo, K., et al., (1982) J. Biochem. 91:1519. They have also been identified in many snake venoms.

Kunitz domains contain six specifically spaced cysteines that are present naturally in disulfide bonds (Bode, W., and Huber, R., (1992) Eur. J. Biochem. 204:433–451). The three disulfide bridges stabilize the protein and are partially responsible for the overall 3-dimensional folding characteristic of a Kunitz domain (FIG. 3). In the 58 residue Kunitz type serine protease BPTI and APPI, cysteines are present at residues 5, 14, 30, 38, 51, and 55. The removal of a one disulfide bridge, however is not accompanied by a large structural change (Eigenbrot, C., et al., (1990) Protein Eng. 3:591–598.

The crystal structure of Kunitz domain type serine protease inhibitors has been determined for BPTI (supra) and APPI (Hynes, T. R., et al., (1990) Biochem., 29:10018–10022). A central anti-parallel three-stranded β-sheet and a C-terminal α-helix form the core of the domain (Bode, W., and Huber, W., supra). The segments of the core domain form the supporting scaffold for the exposed primary binding loop of the properly folded protein (the "primary binding loop" as defined herein)(Bode, W., and Huber, R., supra). A secondary binding loop participates along with the primary binding loop to define the interface between the Kunitz domain and the cognate protease target (the "secondary binding loop" as defined herein)(Ruhlman, A., et al., (1973) J. Mol. Biol. 77:417–436).

"Non-native" as used herein is meant to refer to Kunitz-type domains having an amino acid sequence which is different from the naturally occurring Kunitz domains. Examples of naturally occurring Kunitz domains are, for example, those described in FIG. 2 and in the Description of Related Art. The amino acid sequence of the non-native Kunitz type domains of the present invention differ from the naturally occurring Kunitz domain at least by virtue of the modifications to the primary and secondary binding loops as described herein. In one embodiment the non-natural Kunitz type domain is derived from a naturally occurring Kunitz domain by substitution of one or more amino acids of the naturally occurring Kunitz domain. Such a modification may be made for example by altering the DNA sequence encoding a naturally occurring Kunitz domain. In some instances, the non-native Kunitz-type domain may be derived from a naturally occurring Kunitz type domain by direct chemical modification of one or more of the amino acid side chains of the naturally occurring Kunitz domain.

The "primary binding loop" of a Kunitz domain is designated by $P_5-P_4-P_3-P_2-P_1-P_1'-P_2'-P_3'-P_4'$ (residues 11–19 of BPTI and APPI). The "secondary binding loop" is designated $P_{19}'-P_{20}'-P_{21}'-P_{22}'-P_{23}'-P_{24}'$ (residues 34–39 of BPTI and APPI).

The term "$P_1$" is used herein to refer to the position preceding the scissile peptide bond of the serine protease inhibitors as previously defined by Schecter, L. and Berger, A., (1967) Biochem. Biophys. Res. Commun. 27:157–162. Similarly, the term "$P_1$" is used to refer to the position following the scissile peptide bond of the inhibitor. Increasing numbers refer to the next consecutive position preceding (e.g., $P_2$ and $P_3$) and following (e.g., $P_2'$ and $P_3'$) the scissile bond. The residue numbering corresponds to that of BPTI such that residue $P_{15}$ is at the $P_1$ position.

In the polypeptides of the invention the designations Xaa replace P in referring to amino acid positions. Therefore $Xaa_1$ is equivalent to $P_1$ and $Xaa_1'$ is equivalent to $P_1'$.

APPI refers to the 58 amino acid polypeptide from human Alzeheimer's disease amyloid β-protein precursor, residues 287–344 (Castro, et al., (1990) FEBS Lett. 267:207–212). In this protein $P_5-P_4-P_3-P_2-P_1-P_1'-P_2'-P_3'-P_4'$ corresponds to residues 11–19 of the primary binding loop. $P_{19}'$ corresponds to residue 34 of the secondary binding loop.

The term "amino acid" within the scope of the present invention is meant to refer to naturally occurring L alpha amino acids or residues. The commonly used one and three letter abbreviations for amino acids are used herein (Lehninger, A. L., Biochemistry, 2d ed., pp. 71–92, (1975), Worth Publishers, New York).

The term "conservative" amino acid substitution as used within this invention is meant to refer to amino acid substitutions which substitute functionally equivalent amino acids. Conservative amino acid changes result in silent changes in the amino acid sequence of the resulting protein. For example, one or more amino acids of a similar polarity act as functional equivalents and result in a silent alteration within the amino acid sequence of the protein. Conservative amino acid substitution have been defined as the amino acid substitutions set forth in Table 1 on page 240 of Taylor, W. R., (1986) J. Mol. Biol. 188:233–258. The largest sets of conservative amino acid substitutions include:

(1) hydrophobic: His, Trp, Tyr, Phe, Met, Leu, Ile, Val, Ala;

(2) neutral hydrophilic: Cys, Ser, Thr;

(3) polar: Ser, Thr, Asn, Gln;

(4) acidic/negatively charged: Asp, Glu;

(5) charged: Asp, Glu, Arg, Lys, His (6) basic/positively charged: Arg, Lys, His;

(7) basic: Asn, Gln, His, Lys, Arg;

(8) residues that influence chain orientation: Gly, Pro; and (9) aromatic: Trp, Tyr, Phe, His.

In addition, structurally similar amino acids can substitute for some of the specific amino acids. Groups of structurally similar amino acids include: (Ile, Leu, and Val); (Phe and Tyr); (Lys and Arg); (Gln and Asn); (Asp and Glu); and (Gly, and Ala). Exemplary conservative amino acid substitutions are preferably made in accordance with the following: Gly or Ser for Ala; Lys for Arg; Gln or His for Asn; Glu for Asp; Ser for Cys; Asn for Gln; Asp for Glu; Ala or Pro for Gly; Asn or Gln for His; Leu or Val for Ile; Ile or Val for Leu; Arg, Gln, or Glu for Met; Met, Leu or Tyr for Phe; Thr for Ser; Ser for Thr; Tyr for Trp; Trp or Phe for Tyr; Ile or Leu for Val.

"Expression vector" refers to a DNA construct containing a DNA sequence which is operably linked to a suitable control sequence capable of effecting the expression of the protein encoded by the DNA in a suitable host. Such control sequences generally include a promoter to effect transcription, an optional operator sequence to control transcription, a sequence encoding suitable mRNA ribosome binding sites, and sequences which control termination of transcription and translation. The vector may be a plasmid, a phage particle or "phagemid", or simply a potential genomic insert.

Once transformed into a suitable host, the vector may replicate and function independently of the host genome, or may, in some instances, integrate into the genome itself. In the present specification, "plasmid", "vector" and "phagemid" are sometimes used interchangeably as the plasmid is the most commonly used form of vector at present. However, the invention is intended to include such other forms of expression vectors which serve equivalent functions and which are, or which become, known in the art.

"Operably linked," when describing the relationship between two DNA or polypeptide sequences, simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

Discovery and Preferred Embodiments

The present inventors have discovered that replacement or substitution of certain key amino acids found at positions within and around the primary and secondary binding loops of Kunitz-type serine protease inhibitors can dramatically improve the potency of the inhibitors toward plasma kallikrein. The present invention therefore provides for polypeptides which comprise one or more non-native Kunitz-type domains that are designed to potently inhibit plasma kallikrein.

According to the present invention, residues 11–19, and 34 corresponding to residues $P_5-P_4-P_3-P_2-P_1-P_1'-P_2'-P_3'-P_4'$ and $P_{23}$, of a Kunitz-type serine protease inhibitor are selected from among the naturally occurring amino acids such that potent inhibition of plasma kallikrein is achieved. Of the many interactions between the serine protease subsites and the side chains in the primary binding loop of Kunitz-type domain serine protease inhibitors ($P_5-P_4'$) (Bode, W. and Huber, R., (1992) Eur. J. Biochem. 204:433–451; Laskowski, M., Jr. and Kato, I., (1980) Annu. Rev. Biochem. 49:593–626), the interactions of the $P_1$ residue with the specificity pocket are energetically most important and therefore represent the primary specificity determinants (see FIG. 3). In a Kunitz type domain/serine protease complex, the side chain of residue 15 of the Kunitz-type domain fills the $P_1$ position preceding the scissile peptide bond. According to a preferred aspect of the present invention, plasma kallikrein is potently inhibited by polypeptides comprising a Kunitz-type domain wherein an Arg is found at position 15 ($P_1$). While preferred polypeptides comprise a Kunitz domain with Arg at position $P_1$ Lys is also contemplated at $P_1$.

The crystal structures of Kunitz-type domains reveal other residues within the primary binding loop that are likely to make contact with the serine protease (Hynes, T. R. et al., (1990) supra; Bode, W. and Huber, R., (1992) supra; Kossiakoff, A. A. (1993) et al., Biochem. Soc. Trans.

21:614–618). Although the amino acid at the $P_1$ position generally dominates the affinity of inhibitors for the serine protease active site (Scott, C. F. et al., (1987) Blood 69:1431–1436; Laskowski, M., Jr. and Kato, I., (1980) supra; Beckmann, J. et al., (1988) Eur. J. Biochem. 176:675–682; Sinha, S. et al., (1991) J. Biol. Chem. 266:21011–21013), residues outside this region (11–14 and 16–19 as well as residue 34 of secondary binding loop) are also known to play a role in binding affinity and specificity towards serine proteases (Kossiakoff, A. A. et al., (1993) supra; Roberts, B. L. et al., (1992) Proc Natl Acad Sci USA 89: 2429–2433).

The present inventors have discovered that potent plasma kallikrein inhibitors result when, in addition to an Arg at position 15, amino acid residues at positions 11–14 and 16–19 in the primary binding loop are Ser, Thr, Arg, Leu, Asp, Pro or Glu at position 11 ($P_5$); Gly at position 12 ($P_4$); Gly, Thr, His, Pro, Arg, or Leu, at position 13 ($P_3$) ; Ala or Gly at position 16 ($P_1'$); Ser, Ala, Leu, Asn, or Trp, at position 17 ($P_2'$); His or Ile at position 18 ($P_3'$); and Pro, Tyr, Leu or Trp at position 19 ($P_4'$). The Cys normally present at positions 14 (and 38) of a Kunitz type serine protease inhibitor is maintained. At the secondary binding loop at position 34 ($P_{19}'$) amino acids Phe, Val, Tyr, Trp and Ser are preferred.

More preferably, potent plasma kallikrein inhibitors result when, in addition to an Arg at position 15, amino acid residues at positions 11–14 and 16–19 in the primary binding loop are Asp, Pro or Glu at position 11 ($P_5$); Gly at position 12 ($P_4$); His, Pro, Arg, or Leu, at position 13 ($P_3$); Ala or Gly at position 16 ($P_1'$); Ala, Leu, Asn, or Trp, at position 17 ($P_2'$); His or Ile at position 18 ($P_3'$); and Pro, Tyr, Leu or Trp at position 19 ($P_4'$). The Cys normally present at positions 14 (and 38) of a Kunitz type serine protease inhibitor is maintained. At the secondary binding loop at position 34 ($P_{19}'$) amino acids Val, Tyr, Trp and Ser are preferred.

The present inventors have also discovered that the polypeptides comprising at least one non-native Kunitz type domain which resulted in increased potency for plasma kallikrein, also inhibited the Factor XIa serine protease found in the human plasma. By contrast, the non-natural Kunitz type serine protease inhibitors were not inhibitors of FXIIa, FXa, thrombin, TF-FVIIa, or activated protein C. Additionally, most of the selected Kunitz inhibitor variants inhibited plasmin only slightly however, moderate (>60%) inhibition was observed for selected variants.

According to a preferred aspect of the present invention, the polypeptides of the present invention comprise at least one non native Kunitz type domain and inhibit plasma kallikrein but do not inhibit plasmin. According to this aspect of the present invention, the polypeptides comprise a Kunitz type serine protease inhibitor domain wherein position 11 is Glu, Asp or Pro; positions 12–19 are Gly, His, Cys, Arg, Ala, Ala, His, and Pro, respectively and position 34 of the secondary binding loop is Val, Tyr, or Trp. Especially preferred among this group of polypeptides are polypeptides which comprise a Kunitz type serine protease inhibitor domain wherein position 11 is Asp.

The invention therefore provides for a polypeptide which comprises at least one Kunitz-type domain having a primary and secondary binding loop as described. The remaining residues of the Kunitz type domain are selected from the naturally occurring amino acids such that the overall tertiary structure of the Kunitz type-domain is maintained. Accordingly, the cysteine residues characteristic of the Kunitz type domain are generally maintained at positions 5, 14, 30, 38, 51 and 55.

In a preferred embodiment of the present invention the residues flanking the primary and secondary binding loop of the variant Kunitz type domain are selected from those residues that make up naturally occurring Kunitz type domains. For instance, a typical Kunitz type domain consists of 58 amino acids. According to the present invention amino acid residues 11–19 and 34 are selected as described to achieve potent inhibition of plasma kallikrein. The flanking residues, i.e., residues 1–10, 20–33 and 35–58, in addition to maintaining the proper cysteine residues as described, may be selected from corresponding residues of naturally occurring Kunitz domains such that the proper three-dimensional structure and the desired activity is maintained.

In preferred aspects of the present invention the flanking residues 1–10, 20–33 and 35–58 are selected from the corresponding flanking regions of other Kunitz type serine protease inhibitors well known in the art. Such Kunitz type serine protease inhibitors include those described in FIG. 2. Therefore, in a preferred embodiment, residues 1–10 are selected from VREVCSEQAE (SEQ ID NO: 6), MHSF-CAFKAD (SEQ ID NO: 7), KPDFCFLEED (SEQ ID NO: 8), GPSWCLTPAD (SEQ ID NO: 9), KEDSCQLGYS (SEQ ID NO: 10), TVAACNLPIV (SEQ ID NO: 11), LPNVCAF-PME (SEQ ID NO: 12), and RPDFCLEPPY (SEQ ID NO: 13); residues 20–33 are selected from the group consisting of RWYFDVTEGKCAPF (SEQ ID NO: 14), RFFFNIF-TRQCEEF (SEQ ID NO: 15), RYFYNNQTKQCERF (SEQ ID NO: 16), RFYYNSVIGKCRPF (SEQ ID NO: 17), RYFYNGTSMACETF (SEQ ID NO: 18), LWAF-DAVKGKCVLF (SEQ ID NO: 19), KWYYDPNTKSCARF (SEQ ID NO: 20), RWFFNFETGECELF (SEQ ID NO: 21), and RYFYNAKAGLCQTF (SEQ ID NO: 22); and residues 35–58 are selected from the group consisting of

YGGCGGNRNNFDTEEYCAAVCGSA (SEQ ID NO: 23),

YGGCGGNRNNFDTEEYCMAVCGSA (SEQ ID NO: 24),

YGGCEGNQNRFESLEECKKMCTRD (SEQ ID NO: 25),

YGGCLGNMNNFETLEECKNICEDG (SEQ ID NO: 26),

YSGCGGNENNFTSKQECLRACKKG (SEQ ID NO: 27),

YGGCMGNGNNFVTEKECLQTCRTV (SEQ ID NO: 28),

YGGCQGNGNKFYSEKECREYCGVP (SEQ ID NO: 29),

YGGCGGNENKFGSQKECEKVCAPV (SEQ ID NO: 30),

YGGCGGNSNNFLRKEKCEKFCKFT (SEQ ID NO: 31), and

YGGCRAKRNNFKSAEDCMRTCGGA (SEQ ID NO: 32) which correspond to the equivalent residues in the Kunitz type serine protease inhibitor domains of APPI (residues 1–58) (SEQ ID NO: 34) from human Alzheimer's disease amyloid β-protein precursor, residues 287–344 (Castro, M. et al. (1990) FEBS Lett. 267:207–212); TFPI-KD1 (residues 22–79) (SEQ ID NO: 35), TFPI-KD2 (residues 93–150) (SEQ ID NO: 36), and TFPI-KD3 (residues 185–242) (SEQ ID NO: 37) of human TFPI (tissue factor protein inhibitor or LACI, Broze Jr., G. J. et al., (1990) Biochemistry 29:7539–7546); ITI-KD1 and ITI-KD2, (residues 22–79 and 78–135) (SEQ ID NO: 38 and 39) of human inter-α-trypsin inhibitor, respectively (Vetr, H. et al., (1989) FEBS Lett. 245:137–140); Collagen α 3 (VI) (residues 2899–2956) (SEQ ID NO: 40) Collagen alpha 3 (VI) chain precursor (Chu, M. L. (1990) et al. EMBO J. 9:385–393); HKIB9 (7–60) (SEQ ID NO: 41) Human Kunitz-type protease inhibitor, HKIB9 (Norris, K., in Genbank Database (Dec. 31, 1993, Release 39.0), submitted Jan. 19,1994); BPTI (1–58) (SEQ ID NO: 42), Aprotinin, bovine basic pancreatic trypsin inhibitor (Creighton T. E. and Charles, I. G., (1987) Cold Spring Harbor Symp. Quant. Biol. 52:511–519) as shown in FIG. 2.

According to a preferred aspect of the invention the residues for the primary and secondary binding loop as described above are presented in the context of the flanking regions 1–10 (SEQ ID NO: 6), 20–33 (SEQ ID NO: 14) and 35–58 (SEQ ID NO: 24) of APPI.

It will be understood by those of skill in the art that conservative amino acid substitutions such as those described above can be made throughout the polypeptides as described herein keeping in mind that the resultant polypeptides have the ability to potently inhibit plasma kallikrein as defined herein.

The skilled artisan will recognize that a Kunitz type domain can appear within a larger functional protein. The serine protease inhibitor TFPI, for instance, contains 3 Kunitz-type domains. Therefore, the present invention provides for a polypeptide which comprises at least one Kunitz type domain that can be expected to potently inhibit plasma kallikrein as discussed above.

Determination of Equilibrium Dissociation Constants

According to the present invention the polypeptides comprising one or more non native Kunitz type domains as defined are capable of the potent inhibition of plasma kallikrein. The present inventors have provided for the amino acids that are found in the primary and secondary binding loops of Kunitz type domain variants that can be expected to potently inhibit plasma kallikrein.

Potent inhibition occurs when the polypeptide has an apparent dissociation constant ($K_i^*$) for plasma kallikrein of less than about 500 picomolar (pM). More preferably, the polypeptides of the present invention have a $K_i$ for plasma kallikrein of less than about 300 pM and most preferably less than about 100 pM.

Apparent equilibrium dissociation constants ($K_i^*$) can be determined using methods derived for tight-binding inhibitors (Bieth, J., (1974) Proteinase Inhibitors, vol:463–469; Williams, J. W. and Morrison, J. F., (1979) Methods Enzymol 63:437–467), assuming enzyme and inhibitor form a reversible complex with a 1:1 stoichiometry as has been observed for the interaction of Kunitz domains with serine proteases (Bode, W. and R. Huber, (1992)supra; Laskowski, M., Jr. and I. Kato, (1980) Annu. Rev. Biochem. supra). The data are fit by nonlinear regression analysis to Equation 1:

$$V_i/V_o = 1 - \frac{[E_o] + [I_o] + K_i^* - \sqrt{([E_o] + [I_o] + K_i^*)^2 - (4 \cdot [E_o] \cdot [I_o])}}{2 \cdot [E_o]} \quad (1)$$

where $V_i/V_o$ is the fractional activity (steady-state inhibited rate divided by the uninhibited rate), $[E_o]$ is the total plasma kallikrein active site concentration, and $[I_o]$ is the total inhibitor concentration.

By measuring apparent $K_i^*$ values with other relevant serine proteases found in human plasma, the relative specificities of naturally occurring Kunitz type serine protease inhibitors such as APPI, BPTI as well as polypeptides which comprise one or more non-native Kunitz domain can be determined. To aliquots of serial diluted polypeptide inhibitor, either activated protein C, thrombin, FXa, FXIa, FXIIa, tissue factor-FVIIa or plasmin can be added. After incubation and addition of the appropriate substrate, plots of fractional activity versus inhibitor concentration are generated as described in the Example sections.

According to the present invention selected variants, purified by trypsin affinity chromatography and reverse phase HPLC, potently inhibit plasma kallikrein, with apparent equilibrium dissociation constants ($K_i^*$) of less than about 300 pM.

As a particular example one such mutant, KALI-DY, which differed from APPI at 6 key residues (11Asp, 13His, 17Ala, 18His, 19Pro and 34Tyr), inhibited plasma kallikrein with a $K_i^*$ =15±14 pM, representing an increase in binding affinity of more than 10,000-fold compared to the naturally occurring serine protease inhibitor, APPI.

Similar to naturally occurring Kunitz serine protease inhibitors such as APPI, the variants also inhibited Factor XIa with high affinity, with $K_i^*$ values ranging from ca. 0.3 to 15 nM; KALI-DY inhibited Factor XIa with a $K_i^*$=8.2 ±3.5 nM. KALI-DY did not inhibit plasmin, thrombin, Factor Xa, Factor XIIa, activated protein C, or tissue factor-Factor VIIa. Consistent with the protease specificity profile, KALI-DY and other non-native inhibitors did not prolong the clotting time in a prothrombin time assay, but did prolong the clotting time in an activated partial thromboplastin time assay >3.5-fold at 1 μM.

Clotting Assays

The increased affinity of the polypeptide inhibitors of the present invention for plasma kallikrein relative to native Kunitz type serine protease inhibitors such as BPTI and APPI is reflected in their ability to prolong clotting time in an activated partial thromboplastin time (APTT) assay. Preferred polypetide inhibitors within the present invention prolonged clotting time in the activated partial thromboplastic time assay but not in the prothrombin time (PT)assay. As will be recognized by one skilled in the art, the APTT assay is an indication of a measure of the intrinsic pathway of coagulation. Therefore, in a preferred embodiment polypeptides according to the present invention prolong clotting time in the APTT assay by at least 1 fold and generally between about 2 and 4 fold. In a preferred embodiment the inhibitors of the present invention prolong clotting time by a factor of 3.5 fold.

Chemical Synthesis

One method of producing the Kunitz domain variants involves chemical synthesis of the protein, followed by treatment under oxidizing conditions appropriate to obtain the native conformation, that is, the correct disulfide bond linkages. This can be accomplished using methodologies well known to those skilled in the art (see Kelley, R. F. and Winkler, M. E. in *Genetic Engineering Principles and Methods*, (Setlow, J. K., ed.)., Plenum Press, N.Y., (1990) vol. 12, pp. 1–19; Stewart, J. M. and Young, J. D. (1984) Solid Phase is Peptide Synthesis, Pierce Chemical Co. Rockford, Ill.).

Figure 1:
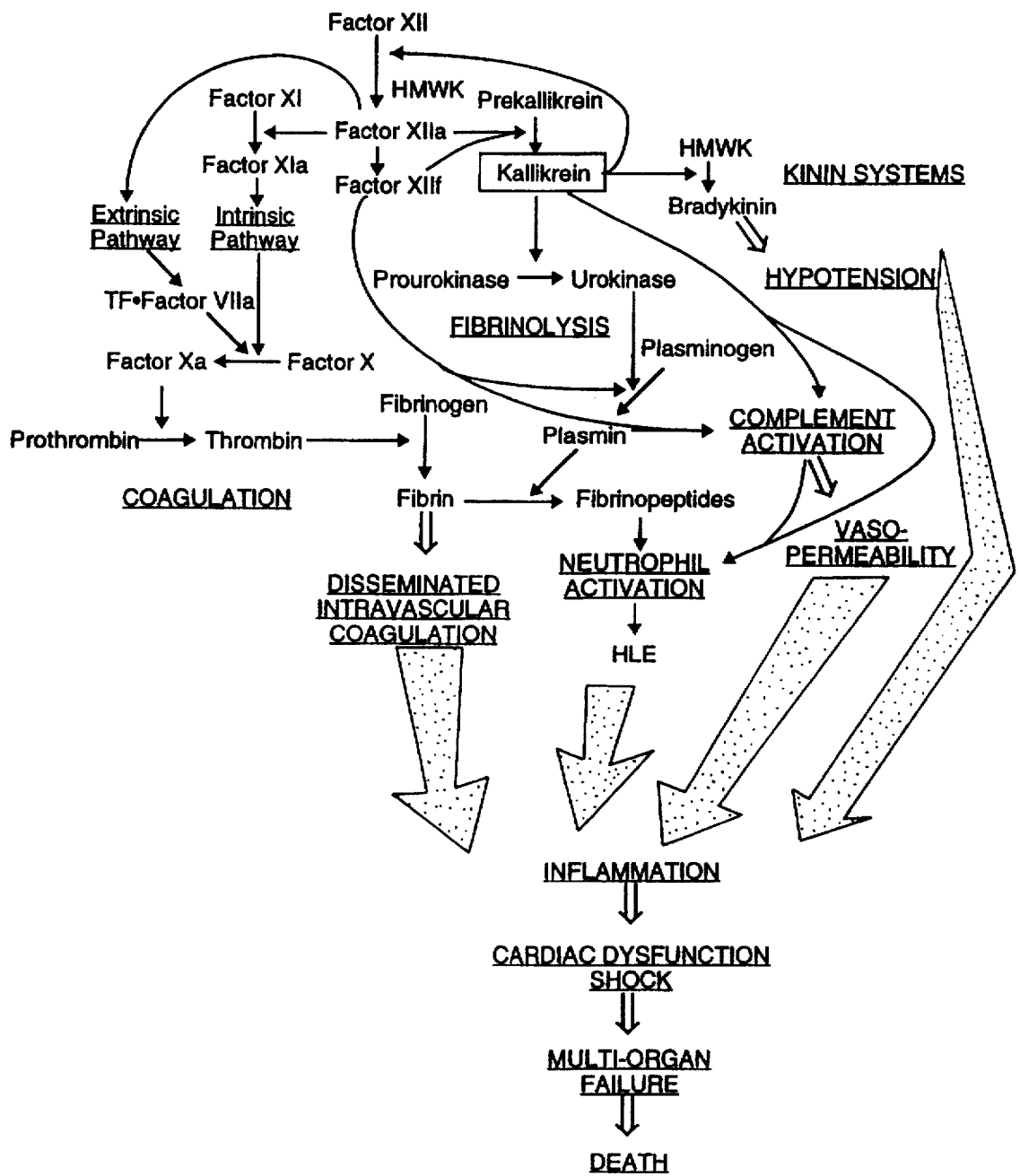
FIG. 1. Schematic outline of selected enzymes and mediators that modulate the coagulation, contact, fibrinolytic, inflammatory, and complement pathways. Activation of these pathways can lead to the clinical states indicated.

Polypeptides of the invention, especially those containing 58 amino acid residues, may be prepared using solid phase peptide synthesis (Merrifield, (1964) J. Am. Chem. Soc., 85:2149; Houghten, (1985) Proc. Natl. Acad. Sci. USA 82:5132). Solid phase synthesis begins at the carboxy-terminus of the putative peptide by coupling a protected amino acid to a suitable resin, as shown in FIGS. 1-1 and 1-2, on pages 2 and 4 of Stewart and Young supra.

In synthesizing polypeptides of this invention, the carboxyl terminal amino acid, with its α-amino group suitably protected, is coupled to a chloromethylated polystyrene resin (see FIG. 1–4, page 10 of Stewart and Young, supra). After removal of the α-amino protecting group with, for example, trifluoroacetic acid (TFA) in methylene chloride and neutralizing in, for example TEA, the next cycle in the synthesis is ready to proceed.

The remaining α-amino- and, if necessary, side-chain-protected amino acids are then coupled sequentially in the desired order by condensation to obtain an intermediate compound connected to the resin. Alternatively, some amino acids may be coupled to one another forming a peptide prior to addition of the peptide to the growing solid phase polypeptide chain.

The condensation between two amino acids, or an amino acid and a peptide, or a peptide and a peptide can be carried out according to the usual condensation methods such as azide method, mixed acid anhydride method, DCC (dicyclohexylcarbodiimide) method, active ester method (p-nitrophenyl ester method, BOP [benzotriazole-1-yl-oxy-tris (dimethylamino) phosphonium hexafluorophosphate] method, N-hydroxysuccinic acid imido ester method), and Woodward reagent K method. In the case of elongating the peptide chain in the solid phase method, the peptide is attached to an insoluble carrier at the C-terminal amino acid. For insoluble carriers, those which react with the carboxy group of the C-terminal amino acid to form a bond which is readily cleaved later, for example, halomethyl resin such as chloromethyl resin and bromomethyl resin, hydroxymethyl resin, aminomethyl resin, benzhydrylamine resin, and t-alkyloxycarbonyl-hydrazide resin can be used.

Common to chemical syntheses of peptides is the protection of the reactive side-chain groups of the various amino acid moieties with suitable protecting groups at that site until the group is ultimately removed after the chain has been completely assembled. Also common is the protection of he α-amino group on an amino acid or a fragment while that entity reacts at the carboxyl group followed by the selective removal of the α-amino-protecting group to allow subsequent reaction to take place at that location. Accordingly, it is common that, as a step in the synthesis, an intermediate compound is produced which includes each of the amino acid residues located in the desired sequence in the peptide chain with various of these residues having side-chain protecting groups. These protecting groups are then commonly removed substantially at the same time so as to produce the desired resultant product following purification.

The applicable protective groups for protecting the α-and ε-amino side chain groups are exemplified by benzyloxy-carbonyl (abbreviated Z), isonicotinyloxycarbonyl (iNOC), O-chlorobenzyloxycarbonyl [Z(NO₂], p-methoxybenzyloxycarbonyl [Z(OMe)], t-butoxycarbonyl, (Boc), t-amyioxycarbonyl (Aoc), isobornyloxycarbonyl, adamatyloxycarbonyl, 2-(4-biphenyl)-2-propyloxycarbonyl (Bpoc), 9-fluorenylmethoxycarbonyl (Fmoc), methylsulfo-nyiethoxycarbonyl (Msc), trifluoroacetyl, phthalyl, formyl, 2-nitrophenylsulphenyl (NPS), diphenylphosphinothioyl (Ppt), dimethylophosphinothioyl (Mpt) and the like.

As protective groups for the carboxy group there can be exemplified, for example, benzyl ester (OBzl), cyclohexyl ester (Chx), 4-nitrobenzyl ester (ONb), t-butyl ester (Obut), 4-pyridylmethyl ester (OPic), and the like. It is desirable that specific amino acids such as arginine, cysteine, and serine possessing a functional group other than amino and carboxyl groups are protected by a suitable protective group as occasion demands. For example, the guanidino group in arginine may be protected with nitro, p-toluenesulfonyl, benzyloxycarbonyl, adamantyloxycarbonyl, p-methoxybenzenesulfonyl, 4-methoxy-2, 6-dimethylbenzenesulfonyl (Mds), 1,3,5-trimethylphenysulfonyl (Mts), and the like. The thiol group in cysteine may be protected with p-methoxybenzyl, triphenylmethyl, acetylaminomethyl ethylcarbamoyl, 4-methylbenzyl, 2, 4, 6-trimethy-benzyl (Tmb) etc, and the hydroxyl group in the serine can be protected with benzyl, t-butyl, acetyl, tetrahydropyranyl, etc.

Stewart and Young, supra provides detailed information regarding procedures for preparing peptides. Protection of α-amino groups is described on pages 14–18, and side-chain blockage is described on pages 18–28. A table of protecting groups for amine, hydroxyl and sulfhydryl functions is provided on pages 149–151.

After the desired amino acid sequence has been completed, the intermediate peptide is removed from the resin support by treatment with a reagent, such as liquid HF and one or more thio-containing scavengers, which not only cleaves the peptide from the resin, but also cleaves all the remaining side-chain protecting groups. Following HF cleavage, the protein sequence is washed with ether, transferred to a large volume of dilute acetic acid, and stirred at pH adjusted to about 8.0 with ammonium hydroxide.

Preferably in order to avoid alkylation of residues in the polypeptide, (for example, alkylation of methionine, cysteine, and tyrosine residues) a thio-cresol and cresol scavenger mixture is used. The resin is washed with ether, and immediately transferred to a large volume of dilute acetic acid to solubilize and minimize intermolecular cross-linking. A 250 µM polypeptide concentration is diluted in about 2 liters of 0.1M acetic acid solution. The solution is then stirred and its pH adjusted to about 8.0 using ammonium hydroxide. Upon pH adjustment, the polypeptide takes its desired conformational arrangement.

Kunitz domains can be made either by chemical synthesis, described above, or by semisynthesis. The chemical synthesis or semisynthesis methods of making allow the possibility of non-natural amino acid residues to be incorporated. This has been carried out for Kunitz domains and described (Beckmann, J. et al., (1988) Eur. J. Biochem. 176: 675–682; Bigler, T. L. et al., (1993) Prot. Sci. 2: 786–799).

For polypeptides containing one or more Kunitz type domains as described herein the chemical ligation techniques described in U.S. Pat. No. 5,403,737 for chemically synthesizing large biomolecules are especially useful.

Mutagenesis and Synthetic Techniques

Various techniques are available which be employed to produce mutant DNA, which can encode the polypeptides of the present invention. For instance, it is possible to derive mutant DNA based on naturally occurring DNA sequences that encode for changes in an amino acid sequence of the resultant protein relative to a native Kunitz type domain such as the APPI molecule. These mutant DNA can be used to obtain the polypeptides of the present invention.

By way of illustration, with expression vectors encoding APPI (Castro et al., supra) or other naturally occurring Kunitz domain polypeptides in hand, site specific mutagenesis (Kunkel et al., (1991) Methods Enzymol. 204:125–139; Carter, P., et al., (1986) Nucl. Acids. Res. 13:4331; Zoller, M. J. et al., (1982) Nucl. Acids Res. 10:6487), cassette mutagenesis (Wells, J. A., et al., (1985) Gene 34:315), restriction selection mutagenesis (Wells, J. A., et al., (1986) Philos. Trans. R. Soc. London Ser A 317, 415) or other known techniques may be performed on the DNA. The mutant DNA can then be used in place of the parent DNA by insertion into the appropriate expression vectors. Growth of host bacteria containing the expression vectors with the mutant DNA allows the production of Kunitz-type serine protease inhibitor variants which can be isolated as described herein.

For polypeptides containing one or more Kunitz type domains as described herein the Kunitz type domain can be ligated into a larger biomolecule using the chemical ligation techniques described in U.S. Pat. No. 5,403,737 for chemically synthesizing large biomolecules for example.

Oligonucleotide-mediated mutagenesis is a preferred method for preparing Kunitz type variants of the present invention. This technique is well known in the art as described by Adelman et al., (1983) DNA, 2:183. Briefly, the native or unaltered DNA of a native Kunitz type domain, for instance APPI, is altered by hybridizing an oligonucleotide encoding the desired mutation to a DNA template, where the template is the single-stranded form of a plasmid or bacteriophage containing the unaltered or native DNA sequence of APPI. After hybridization, a DNA polymerase is used to synthesize an entire second complementary strand of the template that will thus incorporate the oligonucleotide primer, and will code for the selected alteration in the Kunitz domain subunit DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as those described by Crea et al. (1987) Proc. Natl. Acad. Sci. USA, 75:5765.

Single-stranded DNA template may also be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the Kunitz domain, and the other strand (the original template) encodes the native, unaltered sequence of the Kunitz domain. This heteroduplex molecule is then transformed into a suitable host cell, usually a prokaryote such as E. coli 27C7. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-($\alpha$S) (which can be obtained from Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-($\alpha$S) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as E. coli 27C7, as described above.

DNA encoding Kunitz domain variants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions.

The alternative method involves two or more rounds of mutagenesis to produce the desired mutant. The first round is as described for the single mutants: wild-type DNA is used for is the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

A preferred vector for the recombinant expression of Kunitz-domain variants is pSAlz1. This vector, as described in Example 1, contains origins of replication for E. coli, the alkaline phosphatase promoter, the stII signal sequence and an APPI variant gene, and the ampicillin resistance gene. Other preferred vectors are pBO475, pR1T5 and pR1T2T (Pharmacia Biotechnology). These vectors contain appropriate promoters followed by the Z domain of protein A, allowing genes inserted into the vectors to be expressed as fusion proteins. Further discussion of these vectors may be found below.

Other preferred vectors can be constructed using standard techniques by combining the relevant traits of the vectors described herein. Relevant traits of the vector include the promoter, the ribosome binding site, the APPI variant gene or gene fusion (the Z domain of protein A and APPI variant and its linker), the signal sequence, the antibiotic resistance markers, the copy number, and the appropriate origins of replication.

In E. coli, Kunitz domains have been expressed as intact secreted proteins (Castro, M. et al., (1990) FEBS Lett. 267:207–212), intracellularly expressed proteins (Altman, J. D. et al., (1991) Protein Eng. 4:593–600), or as fusion proteins (Sinha, S. et al., (1991) J. Biol. Chem.

266:21011–21013; Lauritzen, C. et al., (1991) Prot. Express. Purif. 2:372–378; Auerswald, E. A. et al.,(1988) Biol. Chem. Hoppe-Seyler 369:27–35).

The host cell may be prokaryotic or eukaryotic. Prokaryotes are preferred for cloning and expressing DNA sequences to produce parent polypeptides, segment substituted polypeptides, residue-substituted polypeptides and polypeptide variants. For example, *E. coli* K12 strain 294 (ATCC No. 31446) may be used as *E. coli* B, *E. coli* X1776 (ATCC No. 31537), and *E. coli* c600 and c600hfl, *E. coli* W3110 (F-,gamma-, prototrophic /ATCC No. 27325), bacilli such as *Bacillus subtilis*, and other enterobacteriaceae such as *Salmonella-typhimurium* or *Serratia marcesans*, and various pseudomonas species. The preferred prokaryote is *E. coli* W3110 (ATCC 27325) as well as the non suppressor derivative 27C7 (ATCC 55,244). When expressed by prokaryotes the polypeptides typically contain an N-terminal methionine or a formyl methionine and are not glycosylated. In the case of fusion proteins, the N-terminal methionine or formyl methionine resides on the amino terminus of the fusion protein or the signal sequence of the fusion protein. These examples are, of course, intended to be illustrative rather than limiting.

In addition to prokaryotes, eukaryotic organisms, such as yeast cultures, or cells derived from multicellular organisms may be used. In principle, any such cell culture is workable. However, interest has been greatest in vertebrate cells, and propagation of vertebrate cells in culture (tissue culture) has become a reproducible procedure (*Tissue Culture*, Kruse and Patterson, eds.(1973) Academic Press). Examples of such useful host cell lines are VERO and HeLa cells, Chinese Hamster Ovary (CHO) cell lines, W138, 293, BHK, COS-7 and MDCK cell lines. Yeast expression systems have been used to make Kunitz domains (Wagner, S. L. et al., (1992) Biochem. Biophys. Res. Commun. 186:1138–1145; Vedvick, T. et al., (1991) J. Indust. Microbiol. 7:197–202). In particular the yeast *Pichia pastoris* has been used successfully using the *Saccharomyces cerevisiae* α mating factor prepro signal sequence and the P. pastoris alcohol oxidase AOX1 promoter and terminator sequences. Other yeast expression vectors and hosts commonly used to express heterologous proteins are also contemplated.

Gene Fusions

A variation on the above procedures contemplates the use of gene fusions, wherein the gene encoding the APPI variant is associated, in the vector, with a gene encoding another protein or a fragment of another protein. This results in the APPI variant being produced by the host cell as a fusion with another protein. The "other" protein is often a protein or peptide which can be secreted by the cell, making it possible to isolate and purify the desired protein from the culture medium and eliminating the necessity of destroying the host cells which arises when the desired protein remains inside the cell. Alternatively, the fusion protein can be expressed intracellularly. It is useful to use fusion proteins that are highly expressed.

The use of gene fusions, though not essential, can facilitate the expression of heterologous proteins in *E. coli* as well as the subsequent purification of those gene products (Harris, T. J. R. in *Genetic Engineering*, Williamson, R., eds.,(1983) Academic, London, Vol. 4, p. 127; Uhlen, M. and Moks, T., (1990) Methods Enzymol. 185:129–143). Protein A fusions are often used because the binding of protein A, or more specifically the Z domain of protein A, to IgG provides an "affinity handle" for the purification of the fused protein (Nilsson, B. and Abrahmsen, L. (1990) Methods Enzymol. 185:144–161). It has also been shown that many heterologous proteins are degraded when expressed directly in *E. coli*, but are stable when expressed as fusion proteins (Marston, F. A. O., (1986) Biochem J., 240:1).

APPI variants expressed as fusion proteins may be properly folded or may require folding to obtain the native structure. The properly folded fusion protein may be active and useful as a serine protease inhibitor. More preferred would be the correctly folded protein that is obtained from the fusion protein by methods known in the art. Fusion proteins can be cleaved using chemicals, such as cyanogen bromide, which cleaves at a methionine, or hydroxylamine, which cleaves between an Asn and Gly. Using standard recombinant DNA methodology, the nucleotide base pairs encoding these amino acids may be inserted just prior to the 5' end of the APPI variant gene.

Alternatively, one can employ proteolytic cleavage of fusion proteins, which has been recently reviewed (Carter, P. in *Protein Purification: From Molecular Mechanisms to Large-Scale Processes*, Ladisch, M. R., Willson, R. C., Painton, C. C., and Builder, S. E., eds., (1990) American Chemical Society Symposium Series No. 427, Ch 13, pp. 181–193).

Proteases such Factor Xa, thrombin, subtilisin and mutants thereof, have been successfully used to cleave fusion proteins. Typically, a peptide linker that is amenable to cleavage by the protease used is inserted between the "other" protein (e.g., the Z domain of protein A) and the protein of interest, such as an APPI variant. Using recombinant DNA methodology, the nucleotide base pairs encoding the linker are inserted between the genes or gene fragments coding for the other proteins. Proteolytic cleavage of the partially purified fusion protein containing the correct linker can then be carried out on either the native fusion protein, or the reduced or denatured fusion protein.

The protein may or may not be properly folded when expressed as a fusion protein. Also, the specific peptide linker containing the cleavage site may or may not be accessible to the protease. These factors determine whether the fusion protein must be denatured and refolded, and if so, whether these procedures are employed before or after cleavage.

When denaturing and refolding are needed, typically the protein is treated with a chaotrope, such as guanidine HCl, and is then treated with a redox buffer, containing, for example, reduced and oxidized dithiothreitol or glutathione at the appropriate ratios, pH, and temperature, such that the protein of interest is refolded to its native structure.

Utility

It has been suggested that the contact activation system plays a significant role in a variety of clinical states including septic shock, cardiopulmonary bypass surgery, adult respiratory distress syndrome, and hereditary angioedema (Bone, R. C., (1992), Arch. Intern. Med. 152:1381–1389; Colman, R. W., (1989) N Engl. J. Med. 320:1207–1209). Inhibitors of the contact system may therefore play important roles in the regulation of inflammatory and/or thrombotic disorders.

The polypeptides described herein are useful in the treatment of diseases where intervention in the activation of the contact pathway or neutrophil activation is indicated (e.g. inflammation, coagulation, fibrinolysis, and complement activation). More specifically, the instant inhibitors are especially useful in the treatment of diseases where inhibition of plasma kallikrein (and FXIa) is indicated (see FIG. 1) as for example in the treatment of sepsis or septic shock, inflammation, ARDS, DIC, hypotension, cardiopulmonary bypass surgery, and for bleeding from postoperative surgery as described in detail in the background section.

The polypeptides described herein are suitably useful in clinical situations that require acute or chronic therapy. It is anticipated that indications for which acute therapy is indicated are more preferred than those for chronic therapy. The pharmaceutical use of foreign or mutant human proteins may be immunogenic; however foreign proteins are used to treat acute indications. An example of such a protein is streptokinase, a protein derived from streptococci that acts as a fibrinolytic and is commonly used to treat acute myocardial infarction. The agents described herein may elicit an immune response; however related foreign proteins such as BPTI have been used in humans clinically and are not anticipated to elicit a serious immune response. The covalent attachment of polyethylene glycol (PEG) to the agents described herein may reduce the immunogenicity and toxicity, and prolong the half-life as has been observed with other proteins (Katre N. V., (1990) J. Immunol. 144:209–213; Poznansky, M. J. et al., (1988) FEB 239:18–22; Abuchowski, A. et al., (1977) J. Biol. Chem. 252:3582–3586)

Aprotinin inhibits the contact, neutrophil, and platelet activation systems during simulated extracorporeal perfusion as evidenced by a reduction in blood loss and kallikrein-C1-inhibitor and C1—C1-inhibitor complexes, as well as prevention of neutrophil degranulation, platelet activation and aggregation (Westaby, S., (1993) Ann. Thor. Surg. 55:1033–1041; Wachtfogel, Y., et al., (1993) J. Thorac. Cardiovasc. Surg. 106:1–10). It has been used during LPS induced endotoxic shock in pigs and prevented arterial hypotension (Seibeck, M., et al., (1993) J. Trauma 34:193–198). In patients with hepatic cirrhosis, aprotinin has resulted in improved renal function and filtration (MacGilchrist A., (1994) Clin. Sci. 87:329–335). The plasma kallikrein Kunitz domain inhibitors described here may be suitably used in the treatment of these and related indications.

The polypeptides of the present invention can be therapeutically useful in the modulation of functions mediated by plasma kallikrien just as aprotinin is used. The present polypeptides offer the advantage of increased potency and specificity for plasma kallikrein allowing for low dose formulations. Effective doses of the polypeptides of the present invention are determined according to the relevant techniques. The selection of compositions, frequency of administration, and amount of composition so administered will be in accordance with the particular disease being treated and its severity, the nature of the polypeptide employed, the overall condition of the patient, and the judgement of the treating physician. Typical dosing regimes will be analogous to treatment of these disease states by the use of other analogous proteins such as aprotinin. Typically, the compositions of the instant invention will contain from about 1% to about 95% of the active ingredient, preferably about 10% to about 50%.

Preferably, the dosing will be by intravenous injection or short term infusion. To acheive optimal therapeutic effect, maintenance dosing may be required. Such maintenance dosing may be given repeatedly during the course of a day by, for instance repeated individual injections or by introduction into a continuous drip infusion.

For intravenous injection or short term infusion, generally between about 1 and 1,000 mg will be administered to an adult and preferably between about 1 and 100 mg. Maintenance dosing at approximately 0.5 to about 50 mg is anticipated.

Other effective dosages can be readily determined by one of ordinary skill in the art through routine trials establishing dose response curves.

Pharmaceutical compositions which comprise the polypeptides of the invention may be administered in any suitable manner, including parental, topical, oral, or local (such as aerosol or transdermal) or any combination thereof. The compositions are preferably administered with a pharmaceutically acceptable carrier, the nature of the carrier differing with the mode of administration, for example, in oral administration, usually using a solid carrier and in I.V. administration, a liquid salt solution carrier.

The compositions of the present invention include pharmaceutically acceptable components that are compatible with the subject and the protein of the invention. These generally include suspensions, solutions and elixirs, and most especially biological buffers, such as phosphate buffered saline, saline, Dulbecco's Media, and the like. Aerosols may also be used, or carriers such as starches, sugars, microcrystalline cellulose, diluents, granulating agents, lubricants, binders, disintegrating agents, and the like (in the case of oral solid preparations, such as powders, capsules, and tablets).

As used herein, the term "pharmaceutically acceptable" generally means approved by a regulatory agency of the Federal or a state government or listed in the U.S. Pharmacopeia or other generally recognized pharmacopeia for use in animals, and more particularly in humans.

The formulation of choice can be accomplished using a variety of the aforementioned buffers, or even excipients including, for example, pharmaceutical grades of mannitol, lactose, starch, magnesium stearate, sodium saccharin cellulose, magnesium carbonate, and the like. "PEGylation" of the compositions may be achieved using techniques known to the art (see for example International Pat. Publication No. WO92/16555, U.S. Pat. No. 5,122,614 to Enzon, and International Pat. Publication No. WO92/00748). Oral compositions may be taken in the form of solutions, suspensions, tablets, pills, capsules, sustained release formulations, or powders.

The present invention has of necessity been discussed by reference to certain specific methods and materials. It is to be understood that the discussion of these specific methods and materials in no way constitutes any limitation on the scope of the present invention, which extends to any and all alternative materials and methods suitable for accomplishing the ends of the present invention.

EXAMPLE 1

Construction and Purification of Plasma Kallikrein Inhibitors Methods

Human Factor VIIa, Factor Xa, Factor XIa, activated protein C, and thrombin were purchased from Haematologic Technologies Inc. (Essex Jct., VT). Human plasma kallikrein and Factor XIIa were purchased from Enzyme Research Laboratories, Inc. (South Bend, Ind). The gene encoding the APPI sequence is described in Castro, M. et al., (1990) FEBS Lett. 267:207–212; recombinant human tissue factor$_{1-243}$ (TF) was produced in $E.\ coli$ as described in Paborsky, L. R., et al., (1989) Biochemistry 28:8072–8077 and Paborsky, L. R., et al., (1991) J. Biol. Chem. 266:21911–21916. BPTI (Trasylol®) was obtained from Boehringer Mannheim (Indianapolis, Ind). Bovine trypsin and TRITONO® X-100 were purchased from Sigma Chemicals, Inc. Bovine serum albumin (BSA), Fraction V was obtained from Calbiochem (La Jolla, Calif.). Human plasmin, S-2302, S-2251, and S-2366 were purchased from Kabi Vitrum (Sweden) and Spectrozyme FXa was purchased from American Diagnostica (Greenwich, Conn.). $E.\ coli$ strain XL1-Blue was from Stratagene (La Jolla, Calif.). All other reagents obtained were of the highest grade commercially available.

The plasmid pSAlz1 was constructed by inserting a synthetic gene encoding the APPI sequence into an appropriate expression vector for secretion of APPI into the periplasm and media. The pSAlz1 vector contained the alkaline phosphatase promoter, stII secretion signal, the APPI gene, the f1 and colE1 origins of replication, and the ampicillin resistance gene as described by Castro et al. (Castro, M. et al., (1990) supra). The construction of APPI mutants using the pSAlz1 vector was accomplished using site-directed oligonucleotide mutagenesis as previously described (Kunkel, T. A. et al., (1991) Methods Enzymol. 204:125–139); selected clones were analyzed by dideoxy sequence analysis (Sanger, F. et al., (1977) Proc. Natl. Acad. Sci. USA 74:5463–5467).

Phagemids encoding either APPI or the selected mutants were transformed into E. coli strain 27C7, a derivative of E. coli W3110, for expression of the Kunitz domain inhibitors. Overnight saturated cultures were inoculated (1%) into 250 ml of low phosphate minimal media (Chang, C. N. et al., (1987) Gene 55:189–196) containing 50 μg/ml ampicillin and grown for 20 h at 37° C.

Inhibitors were secreted into the periplasm by virtue of the stII signal sequence and eventually leaked into the media. Cells and debris were removed by centrifugation (8000 ×g, 10 min); the supernatant was adjusted to pH 7.5 –8.5 with 1M NaOH and then loaded onto a 1 ml trypsin-Affigel 10 (Bio-Rad Laboratories, Richmond, Calif.) affinity column which was prepared according to the manufacturer's recommendations. The column was washed with 100 mM Tris pH 8, 100 mM NaCl, and 20MM $CaCl_2$ and inhibitors were eluted with 4 ml of 10 mM HCl , 0.5M KCl . The inhibitors were further purified using C18 reverse phase HPLC (250 ×4.6 mm, VYDAC); they were loaded in 0.1% trifluoroacetic acid and eluted with a $CH_3CN$ gradient from 5 to 40% at 1 ml/min. Elution profiles were monitored at both $A_{214}$ and $A_{280}$. A single well resolved peak was detected for each inhibitor between 30 to 35% $CH_3CN$. Inhibitor sequences were verified for the proper mass using a Sciex API 3 mass spectrometer equipped with an articulated electrospray source for mass analysis. Multiply charged ions of horse myoglobin (MW=16,951 Da) were used for instrument calibration.

Results

Site-directed mutants were made to investigate the preferred amino acids at positions 11–19 and 34 of a Kunitz domain for the potent inhibition of plasma kallikrein. The site directed mutants of APPI have the general formula: $R_1$-Xaa$_5$-Xaa$_4$-Xaa$_3$-Xaa$_2$-Xaa$_1$-Xaa$_1$'-Xaa$_2$'-Xaa$_3$'-Xaa$_4$'-$R_2$-Xaa$_{19}$'-$R_3$ wherein $R_1$ represents amino acid residues 1–10 of APPI, VREVCSEQAE (SEQ ID NO: 6); $R_2$ represents amino acid residues 20–33 of APPI, RWYFDVTEGK-CAPF (SEQ ID NO: 14); and $R_3$ represents amino acid residues 35 through 58 of APPI, YGGCGGNRNNFDTEEY-CAAVCGSA. The APPI sequence used in this example has an additional mutation of residue 52 so that Met in the native sequence is replaced with Ala. This mutation is not believed to have any effect on inhibitory activity.

The non-naturally occurring Kunitz domains obtained are listed in Table I below.

TABLE I

Sequences of Kunitz Domain Mutants

| Inhibition | Amino Acid Sequence | |
|---|---|---|
| KALI-D | $R_1$DGHCRAAHPR$_2$FR$_3$ | (SEQ ID NO: 45) |
| KALI-DV | $R_1$DGHCRAAHPR$_2$VR$_3$ | (SEQ ID NO: 46) |
| KALI-DY | $R_1$DGHCRAAHPR$_2$YR$_3$ | (SEQ ID NO: 47) |
| KALI-P | $R_1$PGHCRAAHPR$_2$FR$_3$ | (SEQ ID NO: 48) |
| KALI-PV | $R_1$PGHCRAAHPR$_2$VR$_3$ | (SEQ ID NO: 49) |
| KALI-PY | $R_1$PGHCRAAHPR$_2$YR$_3$ | (SEQ ID NO: 50) |
| KALI-E | $R_1$EGHCRAAHPR$_2$FR$_3$ | (SEQ ID NO: 51) |
| KALI-EV | $R_1$EGHCRAAHPR$_2$VR$_3$ | (SEQ ID NO: 52) |
| KALI-EY | $R_1$EGHCRAAHPR$_2$YR$_3$ | (SEQ ID NO: 53) |
| KALI-13 | $R_1$SGHCRAAIPR$_2$FR$_3$ | (SEQ ID NO: 1) |
| KALI-48 | $R_1$TGHCRAAIPR$_2$FR$_3$ | (SEQ ID NO: 2) |
| KALI-8 | $R_1$LGHCRAAIPR$_2$FR$_3$ | (SEQ ID NO: 3) |
| KALI-10 | $R_1$DGPCRAAIPR$_2$FR$_3$ | (SEQ ID NO: 4) |
| KALI-30 | $R_1$EGHCRAAILR$_2$FR$_3$ | (SEQ ID NO: 5) |
| KALI-46 | $R_1$EGRCRASILR$_2$FR$_3$ | (SEQ ID NO: 33) |
| KALI-38 | $R_1$TGPCRALHSR$_2$YR$_3$ | (SEQ ID NO: 43) |
| KALI-42 | $R_1$TGPCRAAHSR$_2$VR$_3$ | (SEQ ID NO: 44) |

The Kunitz domain variants listed in Table I generally led to potent and selective inhibition of plasma kallikrein (see EXAMPLE s 2 and 3).

Other sequences which inhibit plasma kallikrein are described in Table II below.

TABLE II

| Inhibitor | | |
|---|---|---|
| Kali-19 | $R_1$DGHCRAAIPR$_2$FR$_3$ | (SEQ. ID NO: 54) |
| Kali-12 | $R_1$DGPCRAAIPR$_2$FR$_3$ | (SEQ. ID NO: 55) |
| Kali-26 | $R_1$DGPCRAAIPR$_2$IR$_3$ | (SEQ. ID NO: 56) |
| Kali-31 | $R_1$DGRCRAAIPR$_2$FR$_3$ | (SEQ. ID NO: 57) |
| Kali-22 | $R_1$EGTCRANIYR$_2$FR$_3$ | (SEQ. ID NO: 58) |
| Kali-25 | $R_1$LGGCRAWILR$_2$FR$_3$ | (SEQ. ID NO: 59) |
| Kali-7 | $R_1$PGHCRAAIPR$_2$FR$_3$ | (SEQ. ID NO: 60) |
| Kali-29 | $R_1$PGLCRAAFPR$_2$FR$_3$ | (SEQ. ID NO: 61) |
| Kali-23 | $R_1$PGLCRAAIYR$_2$FR$_3$ | (SEQ. ID NO: 62) |
| Kali-21 | $R_1$PGLCRALIWR$_2$FR$_3$ | (SEQ. ID NO: 63) |
| Kali-17 | $R_1$PGRCRAAIPR$_2$FR$_3$ | (SEQ. ID NO: 64) |
| Kali-28 | $R_1$RGHCRAAIPR$_2$FR$_3$ | (SEQ. ID NO: 65) |
| Kali-32 | $R_1$TGPCRAAHSR$_2$VR$_3$ | (SEQ. ID NO: 66) |
| Kali-35 | $R_1$TGPCRAAHSR$_2$YR$_3$ | (SEQ. ID NO: 67) |
| Kali-39 | $R_1$TGPCRGAHSR$_2$VR$_3$ | (SEQ. ID NO: 68) |
| Kali-41 | $R_1$TGPCRGAHSR$_2$WR$_3$ | (SEQ. ID NO: 69) |
| Kali-33 | $R_1$TGPCRALHSR$_2$YR$_3$ | (SEQ. ID NO: 70) |
| Kali-36 | $R_1$TGPCRANHSR$_2$SR$_3$ | (SEQ. ID NO: 71) |

EXAMPLE 2

Determination of Equilibrium Dissociation Constants Methods

Apparent equilibrium dissociation constants ($K_i^*$) were determined for the Kunitz-domain mutants listed in Table I. The $K_i^*$ values were determined using methods derived for tight-binding inhibitors (Bieth, J. (1974) in Proteinase Inhibitors (Fritz, H., Tschesche, H., Greene, L. J., and Truscheit, E., eds), pp. 463–469, Springer-Verlag, New York; Williams, J. W., and Morrison, J. F., (1979) supra), assuming enzyme and inhibitor form a reversible complex with a 1:1 stoichiometry as has been observed for the interaction of Kunitz domains with serine proteases (Bode, W., and Huber, R., (1992) supra; Laskowski, M., Jr., and Kato, I., (1980) supra.

Concentrations of the inhibitor stocks were accurately determined by titration with active site-titrated trypsin (Jameson, G. W., et al., (1973) Biochem. J., 131:107–117). After 1 h incubation of 80 nM trypsin plus an aliquot of diluted inhibitor in 50 mM Tris (pH 8.0), 100 mM NaCl, 10 mM CaCl$_2$ and 0.05% Triton X-100 at room temperature. 20 µl of 5mM N$^\alpha$-benzoyl-L-arginine-p-nitroanilide was added to a total volume of 150 µl. The change in absorbance at 405 nM was then monitored. The concentrations determined assumed a 1:1 stoichiometry of inhibitor with trypsin.

The inhibition of plasma kallikrein by selected APPI mutants (Table I) was determined at 25°C. in 50 mM Tris, pH 7.5, 100 mM NaCl, 2 mM CaCl$_2$ and 0.005% Triton X-100 using an aliquot of the same diluted inhibitor solutions. Reactions (200 µL) were carried out in microtiter plates and the rate substrate (0.7 mM S2302) was monitored at 405 nm following a 1.5 h incubation. Plots of the fractional rate versus inhibitor concentration were fit by nonlinear regression analysis to Equation 1 to determine apparent equilibrium dissociation constants (K$_i$*)

Equation 1:

$$V_f/V_o = 1 - \frac{[E_o] + [I_o] + K_i^* - \sqrt{([E_o] + [I_o] + K_i^*)^2 - (4 \cdot [E_o] \cdot [I_o])}}{2 \cdot [E_o]} \quad (1)$$

where $V_f/V_o$ is the fractional activity (steady-state inhibited rate divided by the uninhibited rate), [E$_o$] is the total plasma kallikrein active site concentration, and [I$_o$] is the total inhibitor concentration.

Results

The Kunitz domain inhibitors described in Table I had apparent dissociation constants in the range of 10 to 300 pM (Table III and Table IV).

The consensus sequence of Table III below consisting of Pro, Asp or Glu at position 11 (P$_5$), His at position 13 (P$_3$), Arg at position 15 (P$_1$), Ala at positions 16 (P$_1$') and 17 (P$_2$'), His at position 18 (P$_3$') , Pro at position 19 (P$_4$') and Val or Tyr at position 34 (P$_{19}$') of APPI was developed based on several observations from the Table II polypeptides, as well as the results presented in Table IV. Variants of APPI with Arg at position 15 (P$_1$) and His, Ala, His and Pro at positions 13, 17, 18 and 19 respectively, were found to potently inhibit plasma kallikrein. In these variants, a preference for Pro, Asp or Glu was observed at position 11 (P$_5$), and at position 34 (P$_{19}$) Val or Tyr were preferred. The cysteine at position 14 (P$_2$) which forms a disulfide bond with the cysteine at position 38 (P$_{23}$') of Kunitz type serine protease inhibitors remained unaltered. Since Gly is almost always found at position 12 (P$_4$) in Kunitz type domains, it was not varied.

In particular, of the consensus type Kunitz domains, mutants containing an Asp at position 11 had apparent equilibrium dissociation constants below 50 pM. One such mutant, KALI-DY, inhibited plasma kallikrein over 10,000-fold better than APPI, and 3,000-fold more potently than BPTI (aprotinin, Trasylol®).

TABLE III

| Inhibitor | Amino Acid Positions | | | | | | | | | | Mass (amu) | | Plasma Kallikrein | FXIa |
|---|---|---|---|---|---|---|---|---|---|---|---|---|---|---|
| | 11 P | 12 | 13 | 14 | 15 | 16 | 17 | 18 | 19 | 34 V | 39 | | | |
| | D | G | H | C | R | A | A | H | P | | | cal | obs | Ki* (nM)$^b$ | Ki* (nM)$^b$ |
| CONSENSUS | E | | | | | | | | | Y | G | | | | |
| KALI-D | D | — | — | — | — | — | — | — | — | F | — | 6377 | 6377 | 0.025 ± 0.022 | 5.7 ± 7.0 |
| KALI-DV | D | — | — | — | — | — | — | — | — | V | — | 6329 | 6328 | 0.043 ± 0.034 | 1.3 ± 1.4 |
| KALI-DY | D | — | — | — | — | — | — | — | — | Y | — | 6393 | 6393 | 0.015 ± 0.014 | 8.2 ± 3.5 |
| KALI-P | P | — | — | — | — | — | — | — | — | F | — | 6359 | 6359 | 0.200 ± 0.099 | 13.8 ± 17.4 |
| KALI-PV | P | — | — | — | — | — | — | — | — | V | — | 6311 | 6310 | 0.166 ± 0.070 | 4.1 ± 5.2 |
| KALI-PY | P | — | — | — | — | — | — | — | — | Y | — | 6375 | 6374 | 0.136 ± 0.081 | 11.7 ± 11.9 |
| KALI-E | E | — | — | — | — | — | — | — | — | F | — | 6391 | 6391 | 0.103 ± 0.054 | 4.5 ± 4.0 |
| KALI-EV | E | — | — | — | — | — | — | — | — | V | — | 6343 | 6343 | 0.117 ± 0.059 | 1.8 ± 1.6 |
| KALI-EY | E | — | — | — | — | — | — | — | — | Y | — | 6407 | 6407 | 0.98 ± 0.075 | 7.3 ± 5.5 |
| APPI | T | G | P | C | R | A | M | I | S | F | G | | | 340 ± 65 | 2.7 ± 1.4 |
| BPTI | T | G | P | C | K | A | R | I | I | V | R | | | 45 ± 4 | >300 |

*Amino acid residues that were mutagenized are shown; "—" indicates that these residues were identical to the consensus. The corresponding sequences of APPI and BPTI are shown for comparison.
$^b$All Ki values reported are from at least 3 independent measurements.

TABLE IV

| Inhibitor | Amino Acid position | | | | | | | | | | Mass (amu) | | Plasma Kallikrein | FXIa |
|---|---|---|---|---|---|---|---|---|---|---|---|---|---|---|
| | 11 | 12 | 13 | 14 | 15 | 16 | 17 | 18 | 19 | 34 | cal | obs | Ki* (nM)$^a$ | Ki* (nM)$^a$ |
| KALI-13 | S | G | H | C | R | A | A | I | P | F | 6385 | 6383 | 0.203 ± 0.039 | 1.4 ± 1.5 |
| KALI-48 | T | G | H | C | R | A | A | I | P | F | 6399 | 6397 | 0.209 ± 0.034 | 0.7 ± 0.5 |
| KALI-8 | L | G | H | C | R | A | A | I | P | F | 6411 | 6412 | 0.074 ± 0.029 | 0.3 ± 0.3 |
| KALI-10 | D | G | P | C | R | A | A | I | P | F | 6373 | 6371 | 0.122 ± 0.051 | 1.5 ± 1.6 |
| KALI-30 | E | G | H | C | R | A | A | I | L | F | 6443 | 6442 | 0.258 ± 0.036 | 0.4 ± 0.5 |
| KALI-46 | E | G | R | C | R | A | S | I | L | F | 6478 | 6476 | 0.175 ± 0.037 | 0.3 ± 0.3 |
| KALI-38 | T | G | P | C | R | A | L | H | S | Y | 6371 | 6369 | 0.259 ± 0.106 | 1.8 ± 1.6 |
| KALI-42 | T | G | P | C | R | A | A | H | S | V | 6265 | 6263 | 0.297 ± 0.170 | 6.6 ± 7.8 |

$^b$All Ki* values reported are from at least 3 independent measurements.

EXAMPLE 3

Specificity Assays

Methods

Figure 4A:
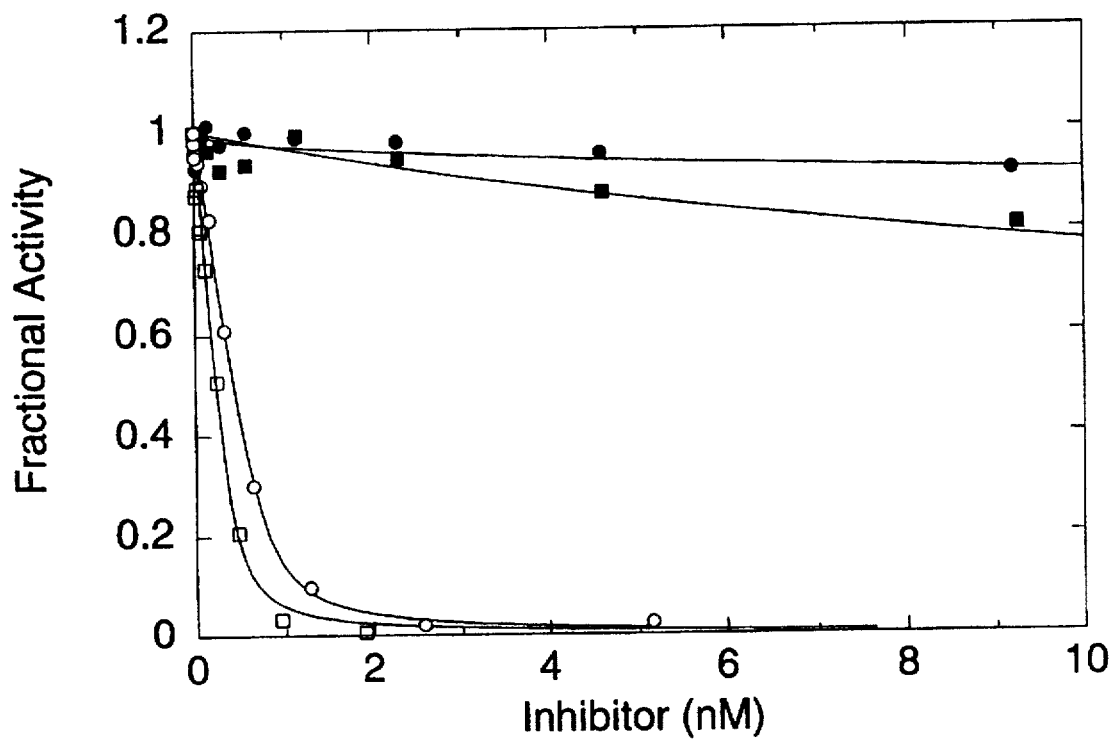
FIG. 4 A and FIG. 4 B. Determination of the apparent equilibrium dissociation constants of selected Kunitz domains with plasma kallikrein and FXIa. The inhibitory activity is expressed as the fractional activity (inhibited rate/uninhibited rate) at varying inhibitor concentrations. The apparent equilibrium dissociation constants were determined by nonlinear regression analysis of the data to equation 1. Shown in FIG. 4 A is the fractional activity of 0.5 nM plasma kallikrein remaining in the presence of: APPI (●), BPTI (■), KALI-10 (○) and KALI-DY (□). Shown in FIG. 4B is the fractional activity of 3.5 nM FXIa remaining in the presence of: APPI (●), BPTI (■), KALI-10 (○) and KALI-DY (□). $K_i$ values are reported in Tables III and IV.
Figure 4B:
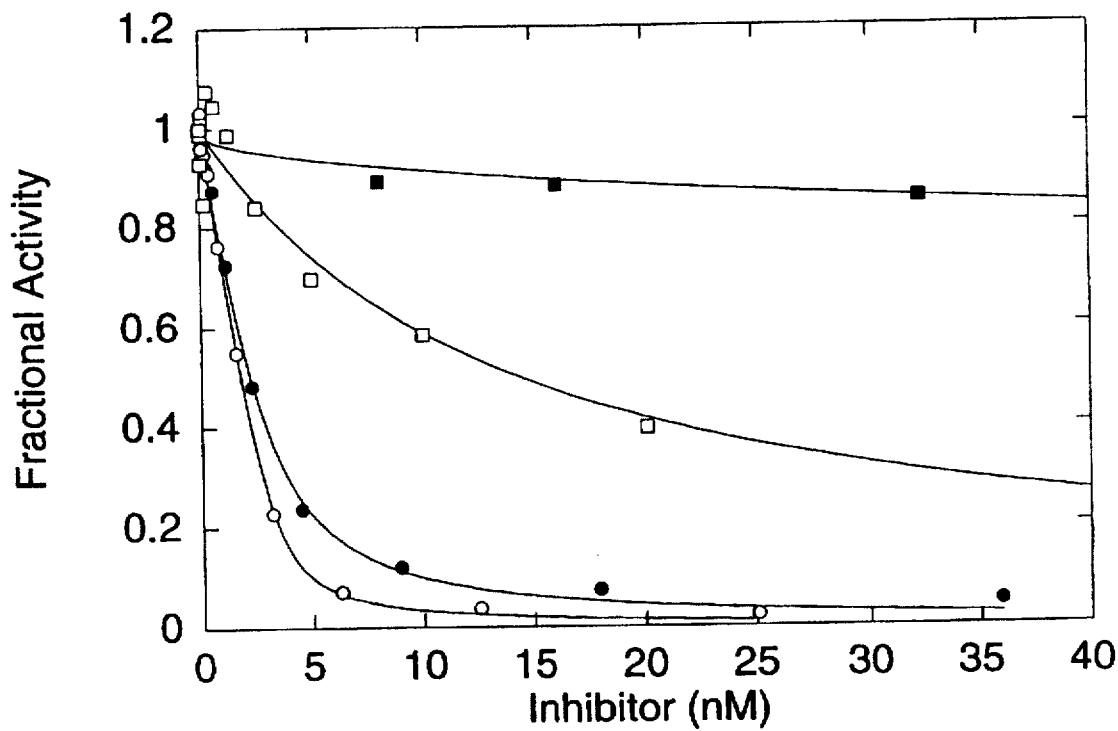

Assays to test the specificity of APPI, BPTI, and Kunitz domain variants against other serine proteases involved in coagulation were conducted using the following format.

tors including the consensus mutants was further investigated by measuring the $K_i$. The inhibition of plasma kallikrein (0.5 nM) in the presence of APPI, BPTI, KALI-D, and KALI-DY is shown in FIG. 4A. The inhibition of FXIa (3.5 nM) by APPI, BPTI, KALI-10 and KALI-DY is shown in FIG. 4B, and $K_i$ values are reported in Tables III and IV.

TABLE V

| Protease[a] | plasma kallikrein | Factor XIa | Factor XIIa | Factor Xa | thrombin | TF · Factor VIIa | plasmin | activated protein C |
|---|---|---|---|---|---|---|---|---|
| BPTI | 0.34 | 0.67 | 1.01 | 0.99 | 0.97 | 1.01 | 0.00 | 0.84 |
| APPI | 0.81 | 0.03 | 0.97 | 0.89 | 0.92 | 0.60 | 0.62 | 0.87 |
| KALI-8 | 0.00 | 0.00 | 1.00 | 1.13 | 0.99 | 0.94 | 0.83 | 0.89 |
| KALI-10 | 0.00 | 0.00 | 0.99 | 1.17 | 0.97 | 0.88 | 0.85 | 0.72 |
| KALI-13 | 0.00 | 0.01 | 1.00 | 0.97 | 0.96 | 0.96 | 0.65 | 0.90 |
| KALI-30 | 0.00 | 0.00 | 0.92 | 0.68 | 1.00 | 1.02 | 0.53 | 0.81 |
| KALI-38 | 0.00 | 0.02 | 0.97 | 0.52 | 1.00 | 0.45 | 0.19 | 0.97 |
| KALI-42 | 0.00 | 0.04 | 0.97 | 0.51 | 0.99 | 0.97 | 0.04 | 0.71 |
| KALI-48 | 0.00 | 0.01 | 0.99 | 0.55 | 0.99 | 0.95 | 0.23 | 0.92 |
| KALI-46 | 0.00 | 0.00 | 0.97 | 1.02 | 0.99 | 0.86 | 0.64 | 0.83 |
| KALI-D | 0.00 | 0.02 | 1.01 | 1.17 | 0.88 | 0.91 | 1.04 | 0.68 |
| KALI-DV | 0.00 | 0.00 | 1.02 | 1.07 | 0.89 | 0.79 | 1.06 | 0.85 |
| KALI-DY | 0.00 | 0.03 | 1.01 | 0.87 | 0.86 | 0.86 | 1.02 | 0.99 |
| KALI-P | 0.00 | 0.12 | 1.02 | 0.99 | 0.85 | 0.93 | 1.05 | 0.52 |
| KALI-PV | 0.00 | 0.07 | 1.04 | 1.15 | 0.92 | 0.83 | 0.74 | 0.80 |
| KALI-PY | 0.00 | 0.13 | 1.02 | 0.91 | 0.98 | 0.94 | 1.06 | 0.91 |
| KALI-E | 0.00 | 0.03 | 1.00 | 0.86 | 0.95 | 0.96 | 1.10 | 0.85 |
| KALI-EV | 0.00 | 0.01 | 0.99 | 0.77 | 0.96 | 0.97 | 1.03 | 1.01 |
| KALI-EY | 0.00 | 0.02 | 0.99 | 0.77 | 1.00 | 1.01 | 1.07 | 1.01 |

Aliquots (30 μL) of various inhibitors diluted to 500 nM were incubated with each protease (100 μL) in the appropriate buffer. After incubation of the substrate/inhibitor mixes at room temperature for 2 h, the appropriate substrate (20 μL) was added, and the absorbance at 405 nm was monitored. Controls lacking inhibitor and enzyme were assayed to measure the uninhibited and substrate hydrolysis rates, respectively. The enzymes and substrates were screened in 50 mM Tris, pH 15 7.5, 100 mM NaCl, 2 mM $CaCl_2$ and 0.005% Triton X-100 as follows: thrombin (6.2 nM), 0.7 mM S2366; FXa (2.5 nM), 0.7 mM Spectrozyme fXa; FXIa (1.8 nM), 0.7 mM S2366; activated protein C (7.6 nM), 0.7 mM S2366; plasmin (32 nM), 0.7 mM S2251; Factor XIIa (14 nM), 0.7 mM S2302, TF (77 nM)-FVIIa (14 nM), 0.7 mM S2366 and plasma kallikrein (3.5 nM), 0.7 mM S2302. The FXIa assay also contained 1 mg/mL BSA. The concentration of FXIa throughout refers to the concentration of active sites. For this experiment, the concentrations of thrombin, TF-FVIIa, FXa, FXIa, FXIIa, and plasmin are 25 approximate and are determined based upon the manufacturers, specifications.

Results

The inhibition of other relevant serine proteases found in human plasma was also measured to determine the relative specificity of the Kunitz domain inhibitors described in Example 2. Serine proteases (1 to 20 nM) were assayed in the presence of 100 nM inhibitor. The fraction of remaining proteolytic activity is reported in Table V. All of the selected Kunitz domains mutants inhibited FXIa, whereas none of them appreciably inhibited FXIIa, FXa, thrombin, TF-FVIIa, or activated protein C (Table V). Most of the selected Kunitz inhibitors inhibited plasmin only slightly and moderate (>60%) inhibition was observed for KALI-38, KALI-42 and KALI-48; however, the consensus mutants of Example 2 (Table III) did not appreciably inhibit plasmin. The degree to which FXIa was inhibited by selected inhibitors including the consensus mutants was further investigated by measuring the $K_i$.

EXAMPLE 4

Coagulation Assays

Methods

Clotting times for normal human plasma were performed using an MLA Electra 800 Coagulometer (Medical Laboratory Automation, Inc. Pleasantville, N.Y.) and Dade reagents (Baxter Health Care Corp., Miami Fla.). The clotting time was determined by optical assessment.

For the activated partial thromboplastin time (APTT) assays, the activation time was set at 120 sec and acquisition time at 300 to 600 sec depending on the expected outcome of the assay. Citrated normal human plasma and inhibitor were incubated together. The sample (plasma and inhibitor) and activator (Actin FS) were automatically pipetted and incubated together for 2 min at 37°C., then $CaCl_2$ was added and clotting time determined by means of optical assessment. The total incubation time of inhibitor with plasma was ca. 3 min before addition of activator, and 5 min before addition of $CaCl_2$.

Results

Figure 5A:
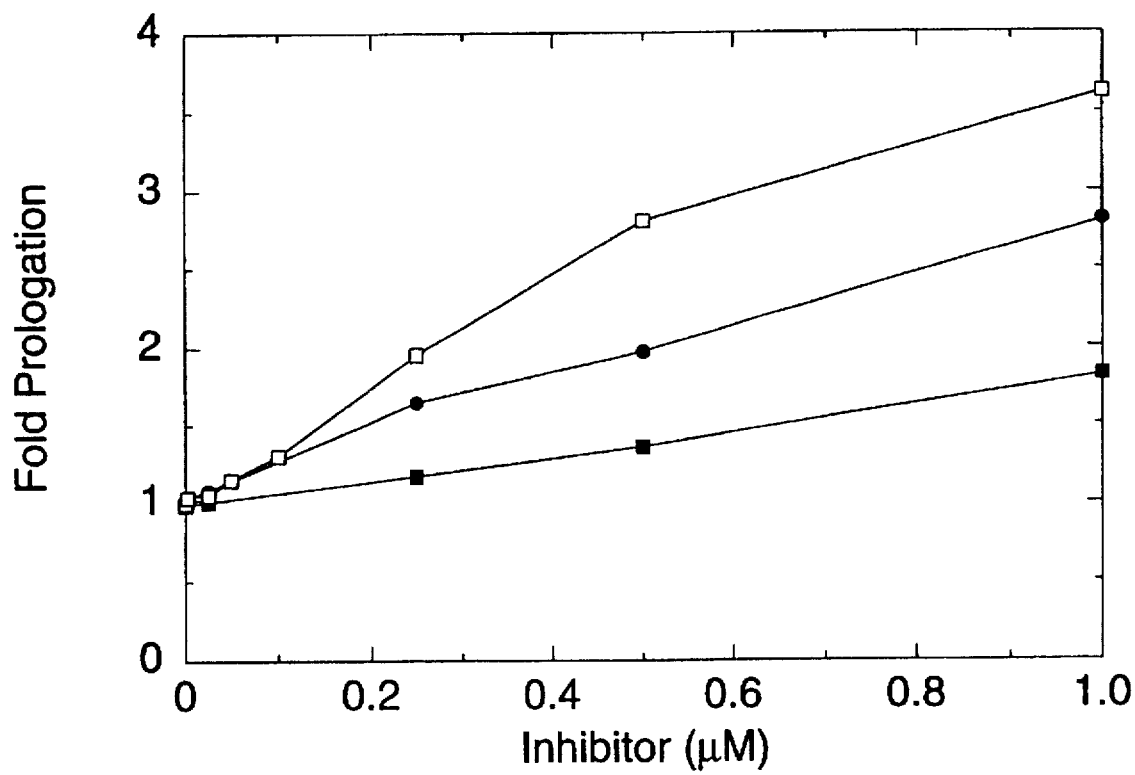
FIG. 5A and FIG. 5B. The concentration of APPI (●), BPTI (■) and KALI-DY (□) are plotted vs. the fold prolongation of clotting time upon initiation by ellagic acid in the APTT assay (FIG. 5A) or by TF membranes in the PT assay (FIG. 5B). The uninhibited clotting times were 33.6 sec and 14 sec for the APTT and PT, respectively.

As predicted from the specificity assays, KALI-DY prolonged the clotting time in the APTT, a measure of the intrinsic coagulation pathway, but not the PT, a measure of the extrinsic coagulation pathway (FIG. 5A). KALI-DY was significantly more effective than either APPI, a FXIa inhibitor ($K_i^* = 2.7$ nM) or BPTI, a kallikrein inhibitor ($K_i^* = 45$ nM). In addition, although plasma prekallikrein is present at 600 nM in plasma, 250 nM KALI-DY can prolong clotting by 2-fold.

Figure 5B:
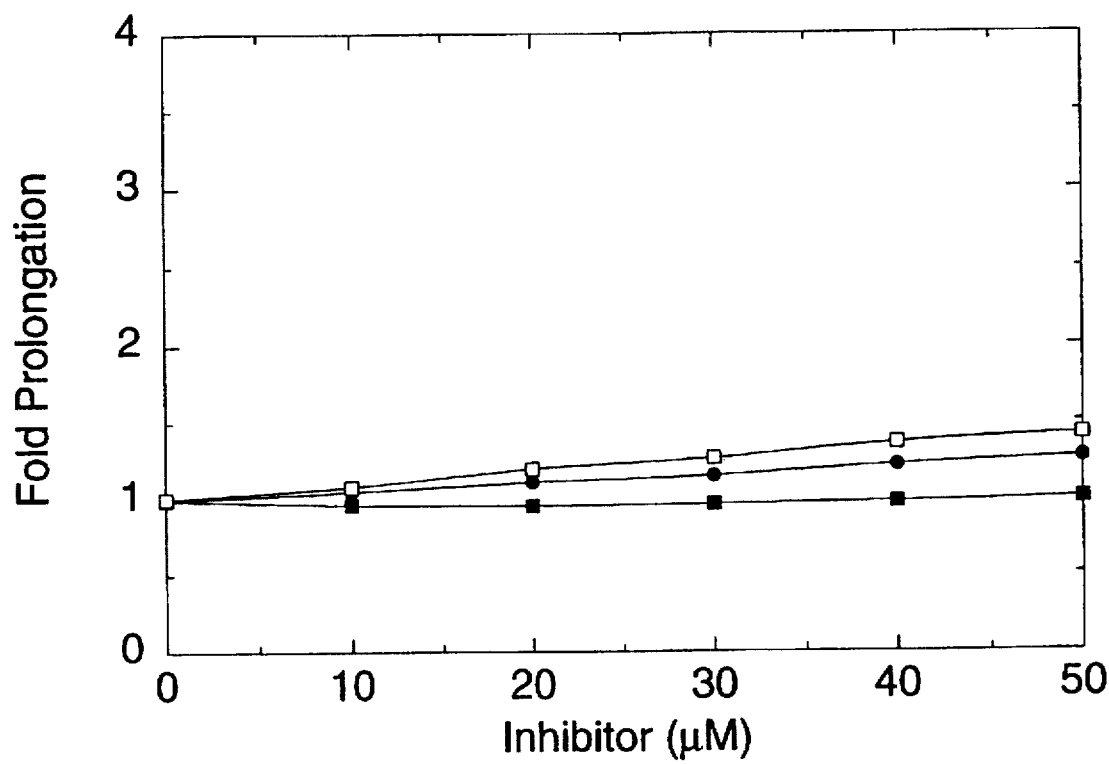

KALI-DY prolonged the clotting time of the surface mediated contact activation pathway in a concentration dependent manner as measured by the APTT. A greater than 3.5-fold prolongation of the clotting time at 1 μM was observed with KALI-DY compared with a 2.8 and 1.8-fold prolongation observed with APPI and BPTI, respectively (FIG. 5A). In contrast, neither KALI-DY, BPTI, nor APPI appreciably prolonged the clotting time in a tissue factor initiated PT assay (FIG. 5B).

All references cited herein are expressly incorporated by reference.

What is claimed is:

1. A method for treating a mammal for which inhibiting plasma kallikrein is indicated comprising administering a therapeutically effective amount of a composition comprising a polypeptide which inhibits plasma kallikrein comprising a non-native Kunitz-type serine protease inhibitor domain of the formula $R_1$-$Xaa_5$-$Xaa_4$-$Xaa_3$-$Xaa_2$-$Xaa_1$-$Xaa_1'$-$Xaa_2'$-$Xaa_3'$-$Xaa_4'$-$R_2$-$Xaa_{19}'$-$R_3$ where $R_1$ is a 10 amino acid peptide wherein the amino acid corresponding to amino acid position $Xaa_{11}$ is a Cys;

$R_2$ is a 14 amino acid peptide wherein the amino acid corresponding to amino acid position $Xaa_{15}'$ is a Cys;

$R_3$ is a 24 amino acid peptide wherein the amino acids corresponding to amino acid positions $Xaa_{23}'$, $Xaa_{36}'$ and $Xaa_{40}'$ are Cys;

$Xaa_5$ is selected from the group consisting of Pro, Asp and Glu;

$Xaa_4$ is Gly;

$Xaa_3$ is Pro;

$Xaa_2$ is Cys;

$Xaa_1$ is Arg;

$Xaa_1'$ is Ala;

$Xaa_2'$ is Ala;

$Xaa_3'$ is His;

$Xaa_4'$ is Pro and $Xaa_{19}'$ is selected from the group consisting of Val, Trp and Tyr and a pharmaceutically acceptable excipient to the mammal.

2. The method according to claim 1 where $R_1$ is selected from the group consisting of SEQ ID NO: 6,
SEQ ID NO: 7,
SEQ ID NO: 8,
SEQ ID NO: 9,
SEQ ID NO: 10,
SEQ ID NO: 11,
SEQ ID NO: 12, and
SEQ ID NO: 13; $R_2$ is selected from the group consisting of
SEQ ID NO: 14,
SEQ ID NO: 15,
SEQ ID NO: 16,
SEQ ID NO: 17,
SEQ ID NO: 18,
SEQ ID NO: 19,
SEQ ID NO: 20,
SEQ ID NO: 21, and
SEQ ID NO: 22; and $R_3$ is selected from the group consisting of
SEQ ID NO: 23,
SEQ ID NO: 24,
SEQ ID NO: 25,
SEQ ID NO: 26,
SEQ ID NO: 27,
SEQ ID NO: 28,
SEQ ID NO: 29,
SEQ ID NO: 30,
SEQ ID NO: 31, and
SEQ ID NO: 32.

3. The method according to claim 2 wherein $R_1$ is SEQ ID NO: 6, $R_2$ is SEQ ID NO: 14 and $R_3$ is SEQ ID NO: 23.

4. The method according to claim 3 wherein the sequence $Xaa_5$-$Xaa_4$-$Xaa_3$-$Xaa_2$-$Xaa_1$-$Xaa_1'$-$Xaa_2'$-$Xaa_3'$-$Xaa_4'$ is SEQ ID NO: 72.

* * * * *